US012640254B2

(12) United States Patent
Ragsdale et al.

(10) Patent No.: US 12,640,254 B2
(45) Date of Patent: May 26, 2026

(54) DATA ROUTING IN COMPUTER NETWORKS USING A HIERARCHICAL USER CLASSIFICATION MODEL

(71) Applicant: Exo Imaging, Inc., Santa Clara, CA (US)

(72) Inventors: Annik Ragsdale, San Jose, CA (US); Michael Pupo, Seattle, WA (US); Ann Lambert, Winnipeg (CA); Sandeep Akkaraju, Wellesely, MA (US); Drake Guenther, Hillsborough, CA (US)

(73) Assignee: Exo Imaging, Inc., Santa Clara, CA (US)

( * ) Notice: Subject to any disclaimer, the term of this patent is extended or adjusted under 35 U.S.C. 154(b) by 313 days.

(21) Appl. No.: 18/135,111

(22) Filed: Apr. 14, 2023

(65) Prior Publication Data

US 2023/0335264 A1 Oct. 19, 2023

Related U.S. Application Data

(60) Provisional application No. 63/331,586, filed on Apr. 15, 2022.

(51) Int. Cl.
 *G16H 40/20* (2018.01)
 *G16H 10/60* (2018.01)
(52) U.S. Cl.
 CPC ............. *G16H 40/20* (2018.01); *G16H 10/60* (2018.01)
(58) Field of Classification Search
 CPC ........ G16H 40/20; G16H 10/60; G16H 30/20; G16H 40/40; G16H 40/60
 USPC ........................................................ 705/2–3
 See application file for complete search history.

(56) References Cited

U.S. PATENT DOCUMENTS

2006/0116913 A1* 6/2006 Hansan .................. G06Q 40/08
 705/4
2018/0189447 A1 7/2018 Khatri et al.
2019/0347387 A1 11/2019 Woodward et al.
2020/0111553 A1* 4/2020 Torres ................... G16H 10/00
2020/0285693 A1* 9/2020 Hatano ................. G06F 40/186

OTHER PUBLICATIONS

Symmetry PACS 1.4.32_P10 User's Manual, 2023, https://healthcare.konicaminolta.us/sites/default/files/2024-04/500-000751A%20SP_1.4.32_P10_UM.pdf (Year: 2023).*
International Search Report and Written Opinion of Application No. PCT/US2021/055890, dated Jan. 26, 2022, 7 pages.
International Search Report and Written Opinion of Application No. PCT/US2023/018743, dated Jul. 21, 2023, 9 pages.

* cited by examiner

*Primary Examiner* — Joy Chng
(74) *Attorney, Agent, or Firm* — Morgan, Lewis & Bockius LLP

(57) ABSTRACT

Point of care ultrasound examinations can be routed and processed in a computer network via the platforms, systems, and methods disclosed herein. The platforms, systems, and/or methods can use computing devices that are configured to provide a client application and at least one server processor for enabling use of an application. The examinations can be managed using an interface that allows an administrator user to assign user roles to other users, which can enable interactions within the network for processing and serving an ultrasound exam object. The ultrasound exam object can include patient data, images, and/or other relevant information.

20 Claims, 27 Drawing Sheets

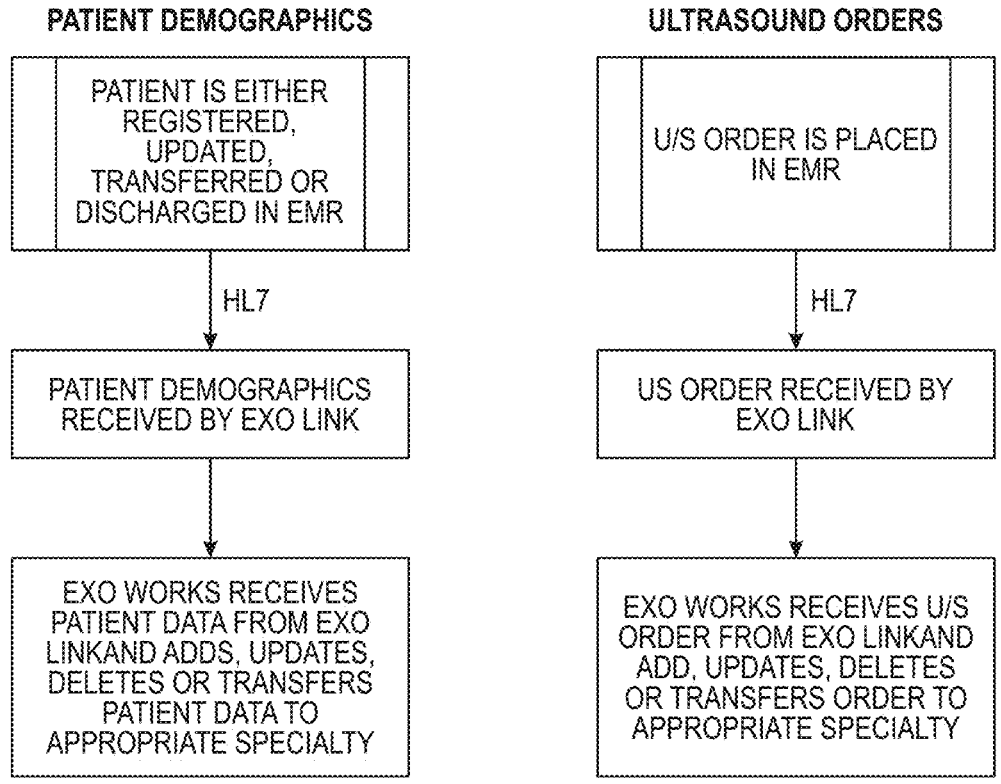
FIG. 2A                    FIG. 2B

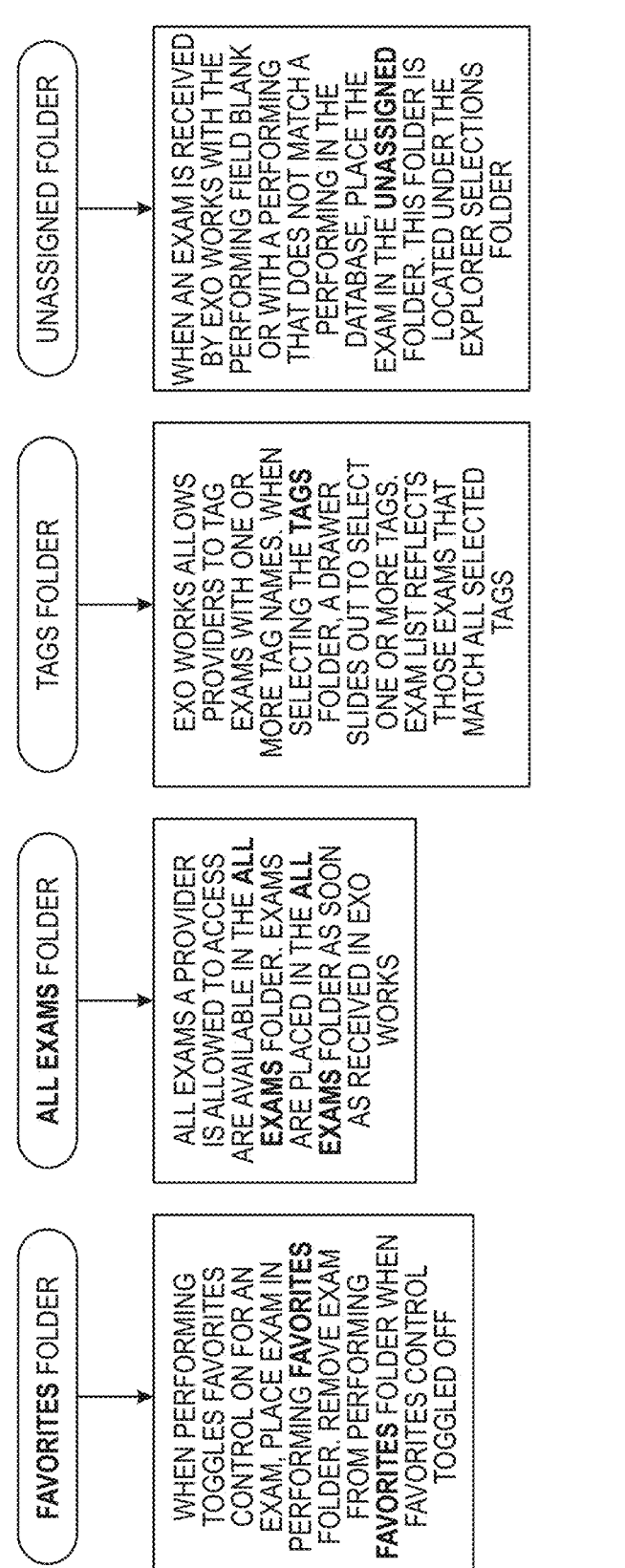

FAVORITES FOLDER

WHEN PERFORMING TOGGLES FAVORITES CONTROL ON FOR AN EXAM, PLACE EXAM IN PERFORMING FAVORITES FOLDER. REMOVE EXAM FROM PERFORMING FAVORITES FOLDER WHEN FAVORITES CONTROL TOGGLED OFF

ALL EXAMS FOLDER

ALL EXAMS A PROVIDER IS ALLOWED TO ACCESS ARE AVAILABLE IN THE ALL EXAMS FOLDER. EXAMS ARE PLACED IN THE ALL EXAMS FOLDER AS SOON AS RECEIVED IN EXO WORKS

TAGS FOLDER

EXO WORKS ALLOWS PROVIDERS TO TAG EXAMS WITH ONE OR MORE TAG NAMES. WHEN SELECTING THE TAGS FOLDER, A DRAWER SLIDES OUT TO SELECT ONE OR MORE TAGS. EXAM LIST REFLECTS THOSE EXAMS THAT MATCH ALL SELECTED TAGS

UNASSIGNED FOLDER

WHEN AN EXAM IS RECEIVED BY EXO WORKS WITH THE PERFORMING FIELD BLANK OR WITH A PERFORMING THAT DOES NOT MATCH A PERFORMING IN THE DATABASE, PLACE THE EXAM IN THE UNASSIGNED FOLDER. THIS FOLDER IS LOCATED UNDER THE EXPLORER SELECTIONS FOLDER

DATA ROUTING IN COMPUTER NETWORKS USING A HIERARCHICAL USER CLASSIFICATION MODEL

CROSS-REFERENCE TO RELATED APPLICATIONS

The present application is a nonprovisional of U.S. Patent App. No. 63/331,586, filed on Apr. 15, 2022, the entirety of which is incorporated herein by reference.

BACKGROUND

Many current technologies for processing medical imaging data, such as ultrasound imaging data, lacks sophistication with respect to user customization and scaling and with respect to the efficiency with which tasks are allocated and organized within a platform, system, or method.

In some cases, end-to-end support for data processing, analysis, review, archiving, and billing is not possible. Instead, technologies must be assembled to perform portions of the overall data handling process. In some cases, these limitations lead to rigid workflow structures that can lead to delays in patient care and, in some cases, to loss of data related to patient medical data.

SUMMARY

In accordance with some embodiments, disclosed herein are platforms, systems, and methods for routing point of care ultrasound examinations in a computer network.

The platform and/or system can be configured to include a plurality of computing devices configured to provide a client application and at least one server processor configured to provide a server application.

In some embodiments, the client application can comprise a user role module configured to present a user interface allowing an administrator user to assign user roles to other users. The user roles can include a performing user, an attending user, and a quality assurance (QA) reviewer user.

The client application can also comprise an ultrasound management module configured to present an interface comprising folders for ultrasound exam objects.

Optionally, the client application can also include an ultrasound review module can be configured to present an interface comprising tools for reviewing ultrasound exam objects.

In some embodiments, the server application can include at least one or more of the following stores and/or modules: a data store, an interface module, an assignment routing module, an interpretation routing module, and a QA routing module.

For example, in some embodiments, the data store can comprise one or more assigned user roles. The interface module can be configured to communicate with at least one ultrasound imaging system and import an ultrasound exam object. The ultrasound exam object can comprise a worksheet and one or more images.

Further, in some embodiments, the assignment routing module can be configured to assign the ultrasound exam object to a performing user. The assignment routing module can also route via the computer network the ultrasound exam object to a performing user's inbox folder to be completed.

In some embodiments, the interpretation routing module can be configured to route via the computer network a completed ultrasound exam object to an attending user's inbox folder to be interpreted. The interpretation routing module can be configured to transfer the completed ultrasound exam object to a performing user's pending folder.

Furthermore, in some embodiments, the QA routing module can be configured to route via the computer network a completed ultrasound exam object to a QA reviewer's inbox folder to be reviewed. The QA routing module can be configured to transfer the completed ultrasound exam object to the performing user's pending folder. The QA routing module can be configured to route via the computer network a reviewed ultrasound exam object to a performing user's flagged folder if the QA reviewer user requests feedback.

Accordingly, in some embodiments, point of care ultrasound examinations can be routed in a computer network by providing a user interface allowing an administrator user to assign user roles to other users.

The users can interact with the network via one or more interfaces that all for the review of ultrasound exam objects and communications with at least one ultrasound imaging system. In some embodiments, the communications can be imported into an ultrasound exam object, for example, to include a worksheet and one or more images.

An assignment routing operation can be performed by assigning the ultrasound exam object to a performing user. Further, the assignment routing operation can include routing via the computer network the ultrasound exam object to a performing user's inbox folder to be completed.

Additionally, the user can perform an interpretation routing operation by routing via the computer network a completed ultrasound exam object to an attending user's inbox folder to be interpreted. The completed ultrasound exam object can be transferred to a performing user's pending folder.

Further, a performing QA routing operation can be performed to route a completed ultrasound exam object to a QA reviewer's inbox folder to be reviewed, via the computer network.

Optionally, the completed ultrasound exam object can be transferred to the performing user's pending folder. Further, the computer network can be used to route a reviewed ultrasound exam object to a performing user's flagged folder if the QA reviewer user requests feedback.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

FIG. 2A shows a non-limiting example of a process comprising incorporating patient demographics information into an exam object, in accordance with some embodiments.

FIG. 2B shows a non-limiting example of a process comprising receiving an exam object order, in accordance with some embodiments.

FIG. 3 shows a non-limiting example of folders useful in the routing of point-of-care examination objects in a computing network, in accordance with some embodiments.

FIG. 18 shows a non-limiting example of a Worksheet Tab of a client application, in accordance with some embodiments.

DETAILED DESCRIPTION

Figure 1A:
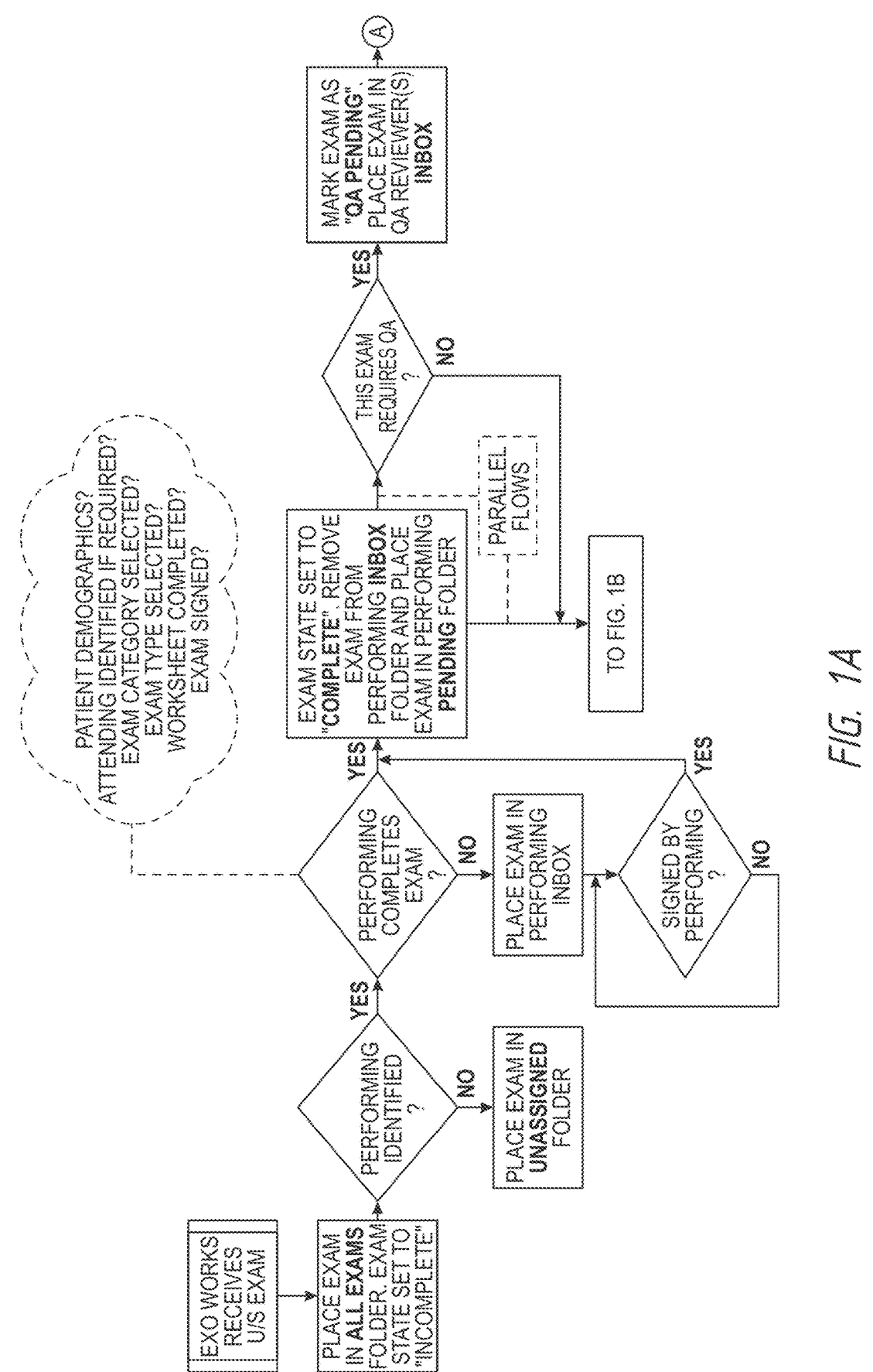
FIG. 1A, FIG. 1B, FIG. 1C, and FIG. 1D show a non-limiting example of a process of routing point of care ultrasound examinations in a computer network, in accordance with some embodiments.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Described herein, in certain embodiments, are platforms for routing point of care ultrasound examinations in a computer network comprising: a plurality of computing devices, each computing device comprising at least one processor and instructions executable by the at least one processor to provide a client application comprising a user role module configured to present a user interface allowing an administrator user to assign user roles to other users, the user roles comprising a performing user, an attending user, and a quality assurance (QA) reviewer user; an ultrasound management module configured to present an interface comprising folders for ultrasound exam objects, the folders comprising an inbox folder, a pending folder, and a flagged folder; and an ultrasound review module configured to present an interface comprising tools for reviewing ultrasound exam objects; and at least one server processor and instructions executable by the at least one server processor to provide a server application comprising a data store comprising one or more assigned user roles; an interface module configured to communicate with at least one ultrasound imaging system and import an ultrasound exam object, the ultrasound exam object comprising a worksheet and one or more images; an assignment routing module configured to: assign the ultrasound exam object to a performing user, and route via the computer network the ultrasound exam object to a performing user's inbox folder to be completed; an interpretation routing module configured to: route via the computer network a completed ultrasound exam object to an attending user's inbox folder to be interpreted, and transfer the completed ultrasound exam object to a performing user's pending folder; and a QA routing module configured to: route via the computer network a completed ultrasound exam object to a QA reviewer's inbox folder to be reviewed, transfer the completed ultrasound exam object to the performing user's pending folder, and route via the computer network a reviewed ultrasound exam object to a performing user's flagged folder if the QA reviewer user requests feedback.

Also described herein, in certain embodiments, are computer-implemented systems for routing point of care ultrasound examinations in a computer network comprising at least one processor and instructions executable by the at least one processor to provide an application comprising: a user role module configured to present a user interface allowing an administrator user to assign user roles to other users, the user roles comprising a performing user, an attending user, and a quality assurance (QA) reviewer user; a data store comprising one or more assigned user roles; an ultrasound management module configured to present an interface comprising folders for ultrasound exam objects, the folders comprising an inbox folder, a pending folder, and a flagged folder; an ultrasound review module configured to present an interface comprising tools for reviewing ultrasound exam objects; an interface module configured to communicate with at least one ultrasound imaging system and import an ultrasound exam object, the ultrasound exam object comprising a worksheet and one or more images; an assignment routing module configured to: assign the ultrasound exam object to a performing user, and route via the computer network the ultrasound exam object to a performing user's inbox folder to be completed; an interpretation routing module configured to: route via the computer network a completed ultrasound exam object to an attending user's inbox folder to be interpreted, and transfer the completed ultrasound exam object to a performing user's pending folder; and a QA routing module configured to: route via the computer network a completed ultrasound exam object to a QA reviewer's inbox folder to be reviewed, transfer the completed ultrasound exam object to the performing user's pending folder, and route via the computer network a reviewed ultrasound exam object to a performing user's flagged folder if the QA reviewer user requests feedback.

Also described herein, in certain embodiments, are computer-implemented methods of routing point of care ultrasound examinations in a computer network comprising: providing a user interface allowing an administrator user to assign user roles to other users, the user roles comprising a performing user, an attending user, and a quality assurance (QA) reviewer user; maintaining a data store comprising one or more assigned user roles; providing an interface comprising folders for ultrasound exam objects, the folders comprising an inbox folder, a pending folder, and a flagged folder; providing an interface comprising tools for reviewing ultrasound exam objects; configuring a communications link with at least one ultrasound imaging system; importing via the communications link an ultrasound exam object comprising a worksheet and one or more images; performing an assignment routing operation comprising assigning the ultrasound exam object to a performing user, and routing via the computer network the ultrasound exam object to a performing user's inbox folder to be completed; performing an interpretation routing operation comprising routing via the computer network a completed ultrasound exam object to an attending user's inbox folder to be interpreted, and transferring the completed ultrasound exam object to a performing user's pending folder; and performing QA routing operation comprising routing via the computer network a completed ultrasound exam object to a QA reviewer's inbox folder to be reviewed, transferring the completed ultrasound exam object to the performing user's pending folder, and routing via the computer network a reviewed ultrasound exam object to a performing user's flagged folder if the QA reviewer user requests feedback.

The quality and/or speed with which medical data (e.g., medical data comprising ultrasound imaging data) is processed can be improved by computer-implemented systems and methods comprising a responsive hierarchical user classification platform, as described herein.

For example, systems and methods described herein, which can involve collection, distribution, modification, and/or review of medical data (e.g., comprising ultrasound imaging data) between various professional and/or administrative users, can lead to administrative delay, decreased data integrity, and/or decreased quality of patient care.

Platforms, systems or methods described herein can provide a hierarchical user structure for review and/or analysis of medical data comprising ultrasound imaging data. For instance, platforms, systems, and methods described herein can be useful in routing point of care ultrasound examination data (e.g., comprising one or more exam objects) in a computer network. In some cases, a system or method described herein can comprise a plurality of computing devices and at least one server processor connected to a computer network, wherein each of the computing devices is configured to provide a client application and wherein the at least one server processor is configured to provide a server application, the server application comprising one or more computer-implemented modules for transmission of data (e.g., comprising ultrasound imaging data, metadata associated with ultrasound imaging data, and/or user-generated data pertaining to the ultrasound imaging data) between the plurality of computing devices, for example, based at least in part on one or more user roles instituted and/or managed via the system or method.

Ultrasound Examination Object Review, Assignment Routing, Analysis, and Interpretation The platforms, systems, and methods described herein can, in some embodiments, comprise a server application and/or a client application, which can be configured or used for receiving, routing, processing, modifying, analyzing, interpreting, maintaining, or archiving an ultrasound examination object (e.g., "exam object") and/or assigning user roles with respect to the processing, modifying, analyzing, or interpreting of the examination object.

Referring to FIG. 1A, the practice of a system or method described herein can comprise receiving an exam object (e.g., comprising one or more worksheets and/or one or more images, which may include one or more static images and/or one or more video images and may comprise one or more (static and/or video) ultrasound images). In some cases, an exam object (e.g., a worksheet of an exam object) can comprise patient data, exam data (e.g., data or measurements produced during an ultrasound imaging examination and/or comments or analysis provided by a user, such as a performing user and/or an attending user), quality assurance (QA) data (e.g., comprising feedback, such as comments and/or scoring, from a QA reviewer).

An exam object can be received by a server application of the system or method, e.g., wherein the server processor receives the exam object via a network (e.g., a telecommunication network or local area network) connection. For instance, an exam object can be received by (e.g., imported by) an interface module of a server application via the network connection. In some cases, an exam object can be received (e.g., by the interface module of the server application) from an imaging system (e.g., at least one imaging system), such as an ultrasound imaging system (e.g., comprising an ultrasound imaging device).

A platform, system, or method described herein can comprise at least one server processor and instructions executable by the at least one server processor to provide (e.g., instantiate via the server processor) the server application. A server application can be in communication with one or more computing devices of the platform, system, or method. For instance, a server application (e.g., or a module thereof) can be in communication with a client application of one or more of a plurality of computing devices of the platform, system, or method.

In some cases, a server application (e.g., or a module thereof) can be in communication with one or more client application modules of one or more computing devices of the plurality of computing devices (e.g., via a network connection). In many cases, a computing device (e.g., each computing device of a plurality of computing devices) of a platform, system, or method described herein can comprise at least one processor and instructions executable by the at least one processor to provide (e.g., instantiate via the at least one processor) a client application comprising one or more client application modules.

In many cases, a server application can be used to route (e.g., transmit and/or receive) data (e.g., comprising one or more exam objects) from a first computing device, client application, client application module, or data store and a second computing device, client application, client application module, or data store of a platform, system, or method described herein.

In some cases, an exam object can be stored permanently or temporarily in a data store of one or more computing devices of the platform, system, or method (e.g., a memory or data store of a client application) or a data store of the server application (e.g., for access or subsequent routing of the exam object by the server application to one or more server application modules and/or one or more computing devices or client applications of the one or more computing devices of the platform, system, or method). In some cases, data received by a server application and/or a client application can be stored in a folder (e.g., of a data store).

In some cases, an exam object can be stored (e.g., placed) in an All Exams folder of a data store (e.g., of a server application or a computing device), for example, after receipt of the exam object (e.g., via an interface module of a server application, for instance, from an ultrasound imaging device or other external source, such as an email address or database (e.g., an Electronic Medical Records (EMR) database). In some cases, an exam object can be stored (e.g., placed) in an All Exams folder of an ultrasound management module of a client application. In some cases, an exam object of a platform, system, or method described herein can be assigned an Exam State. In some cases, an exam object of a platform, system, or method described herein can be assigned an Exam State (e.g., an Exam State of "incomplete") upon initial receipt of the exam object at the All Exam folder.

In some cases, routing of an exam object (e.g., by a server application) can be context dependent, for example, as shown in FIGS. 1A, 1B, 1C, and 1D. In some cases, a server application can route an exam object to an "Unassigned" folder (e.g., of a server application or client application), for instance if a "performing user" (e.g., an individual assigned a "performing" user role) has not yet been identified with respect to the exam object or associated with the exam object.

In some cases, an individual assigned an "attending" user role or an "administrator" user role can be allowed access to the "Unassigned" folder and/or can be provided with privileges that can include adding or modifying the assigned user value of an exam object. In some cases, an attending user and/or an administrator user can add or modify an assigned user role to identify (e.g., and associate) a performing user with the exam object.

In some cases, identifying, assigning, or associating a performing user with the exam object (e.g., via input from an attending user and/or an administrator user) can cause the server application to proceed to a check to determine whether one or more tasks have been completed by the identified, assigned, or associated performing user with respect to the exam object.

In some cases, a server application can check an exam object for which a performing user has been identified, assigned, or associated to determine whether the performing user has completed one or more tasks (e.g., analysis of the exam object and/or input of optional or required information for the exam object) with respect to the exam object.

In some cases, optional or required information for the exam object can include data related to patient biographical or demographic information, identification of an assigned "attending" user, an exam category, an exam type, and/or analysis or observations related to one or more exam object images. If the performing user has failed to complete one or more (e.g., all) tasks with respect to the exam object, the server application can route the exam object to a "Performing Inbox" folder. Subsequent to routing (e.g., placing) the exam object in the Performing Inbox folder of the performing user assigned to the exam object, the server application can check the exam object to determine whether an authorized signature of the performing user is included in the exam object (e.g., upon prompting from the performing user, upon prompting by an attending user, upon prompting by an administrator user, and/or at a predetermined time relative, e.g., relative to the time at which the exam object was placed in the Performing Inbox folder.

In some cases, an exam object can be left in the Performing Inbox associated with the assigned, identified, or associated performing user if the server application determines that the exam object does not include an authorized signature of the assigned, identified, or associated performing user.

In some cases, an Exam State of an exam object can be changed to "Complete" (e.g., via a server application) if a check for an authorized signature of an assigned, identified, or associated performing user and/or one or more optional or required tasks have been performed with respect to the exam object by the performing user (e.g., which may comprise adding or modifying information associated with the exam object, for instance, including data of a worksheet of the exam object).

In some cases, an exam object can be routed to (e.g., placed in) a Performing Pending folder of a server application, client application, or data store after a server application determines that one or more of an authorized performing user signature is present in the exam object and/or one or more optional or required tasks have been completed with respect to the exam object (e.g., by the performing user assigned, identified, or associated with the exam object).

In some cases, a server can perform a check with respect to whether the exam object is identified as requiring quality assurance (QA) review. In some cases, information regarding whether an exam object requires QA review can be included in the exam object.

Figure 1B:
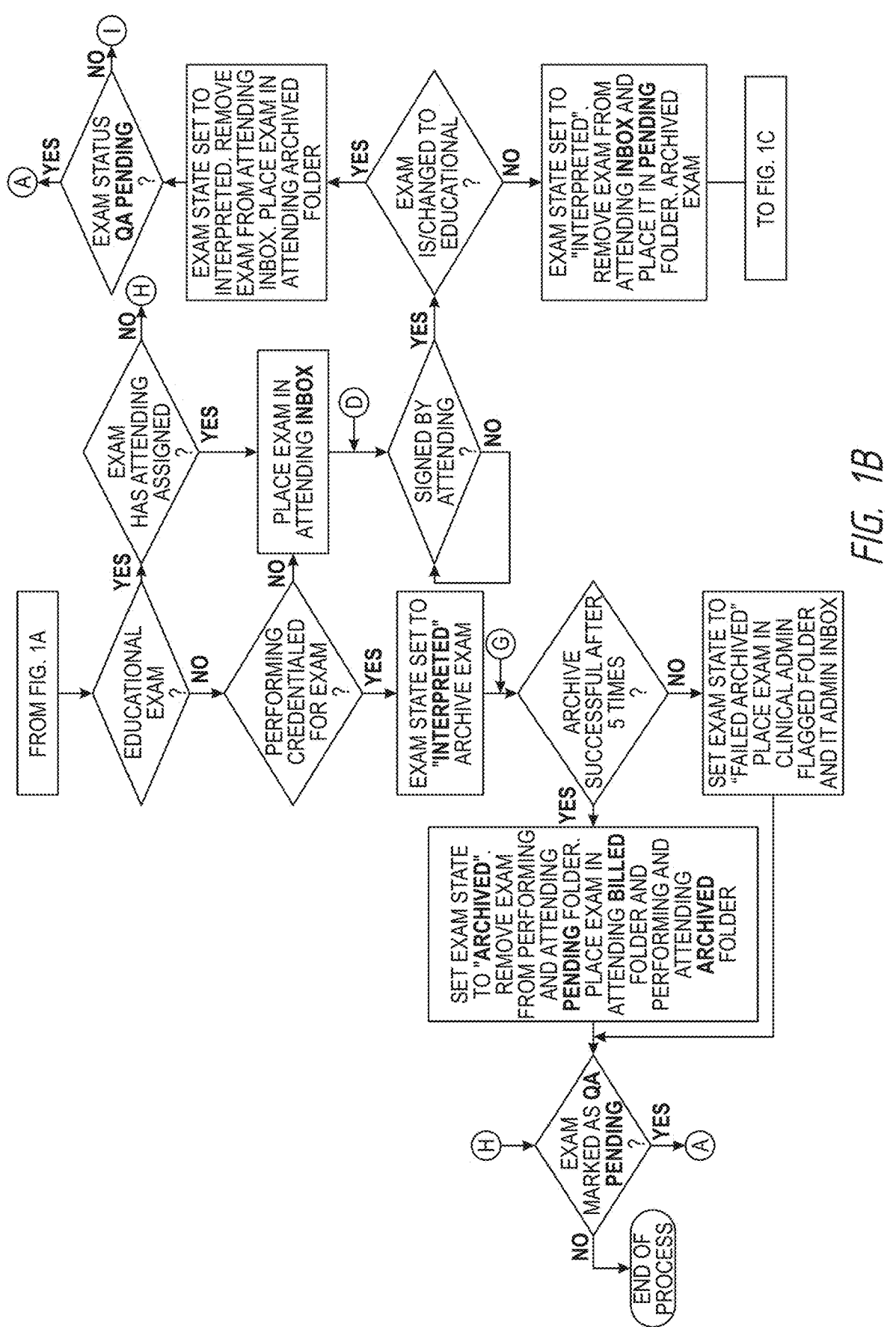

In some cases, information regarding whether an exam object requires QA review can be added and/or modified (e.g., via a server application and/or a client application), for instance, by an attending user and/or an administrator user. If the server application is configured to perform a check as to whether the exam object requires QA analysis and the result is "no" or if the server application is not configured to perform a check as to whether the exam object requires QA analysis, a server application can perform one or more additional checks, change an Exam State of the exam object, and/or route the exam object to one or more locations (e.g., folders), for example, as shown in FIG. 1B. If the server application is configured to perform a check as to whether the exam object requires QA analysis and the result is "yes", the exam object can be routed to (e.g., placed in) one or more "QA Reviewer Inbox" folder and/or an Exam State of the exam object can be changed (e.g., updated) to "QA Pending." In some cases, an exam object can be subjected to QA review (e.g., a QA Process, which can include one or more steps shown in FIG. 1C and/or FIG. 1D following workflow node "A" of FIGS. 1A and 1B).

As discussed above, a server application can perform one or more additional checks, change an Exam State of the exam object, and/or route the exam object to one or more locations (e.g., folders) if the server application is configured to perform a check as to whether the exam object requires QA analysis and the result is "no" or if the server application is not configured to perform a check as to whether the exam object requires QA analysis.

In some cases, a server application can perform a check as to whether the exam object is designated as an Educational Exam (e.g., as shown in FIG. 1B). For instance, an exam object can be used for clinical purposes (e.g., for evaluation or diagnosis of a patient in need thereof) in some embodiments (e.g., wherein the exam object can be a type with a value of "clinical").

In some embodiments, an exam object can be used for educational (e.g., instructional, pedagogical, or academic) purposes (e.g., wherein the exam object can be a type with a value of "educational"). If the exam object is not designated as an Educational Exam (e.g., the Educational Exam check result is "no", for example, wherein the exam object is a type with a value of "clinical"), a subsequent Credential check can be performed by the server application to determine whether the performing user assigned, identified, or associated with the exam object is credentialed for the Exam. In some cases, the exam object can be routed to an Attending Inbox folder associated with an attending user assigned to the exam object if the Credential check result is "no".

In some cases, a check can be performed by the server application subsequent to the Educational Exam check (e.g., if the result of the Educational Exam check is "yes", for example, wherein the exam object is a type with a value of "educational") to determine whether an attending user has been assigned to the exam object.

Figure 1C:
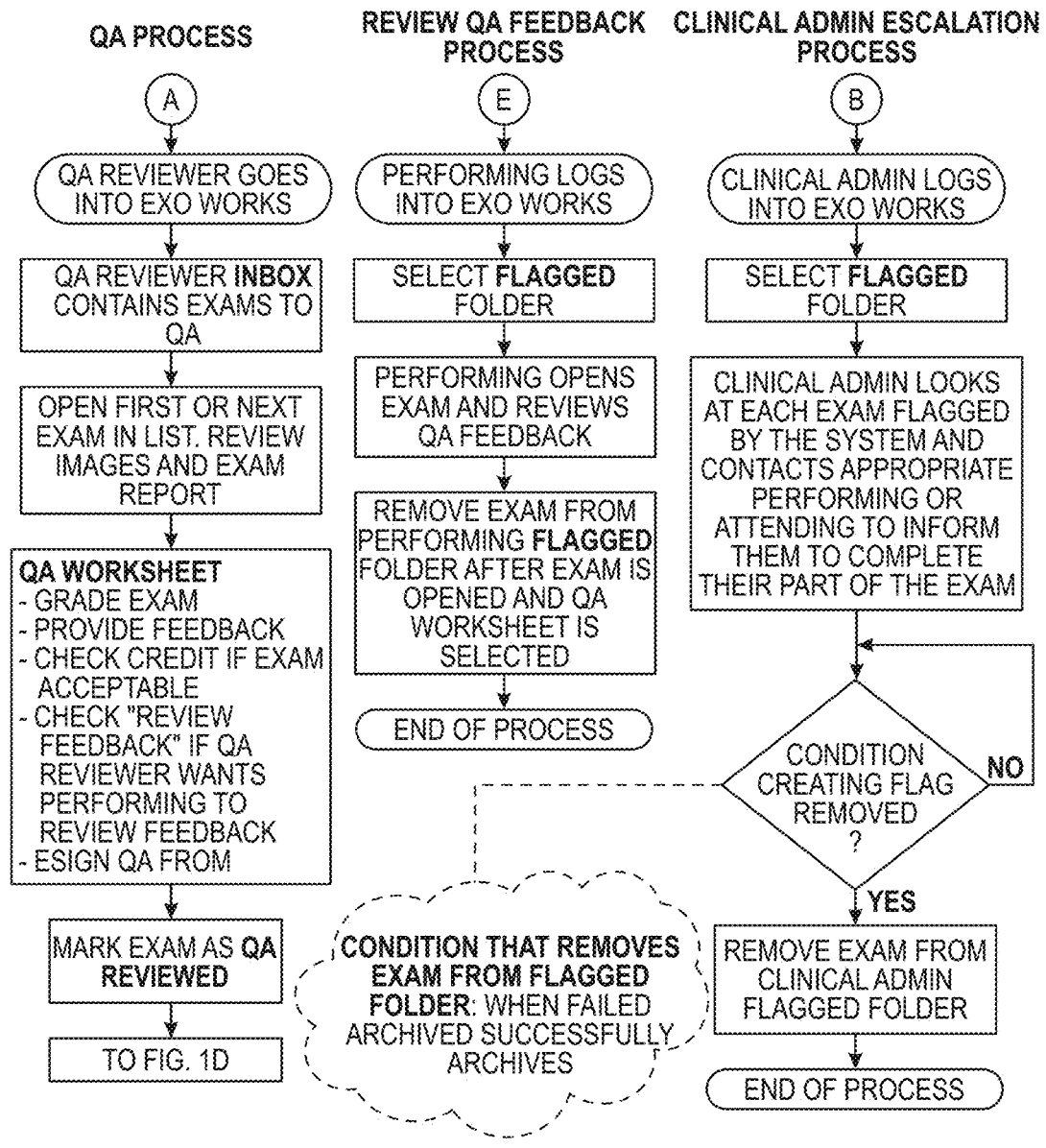
Figure 1C:
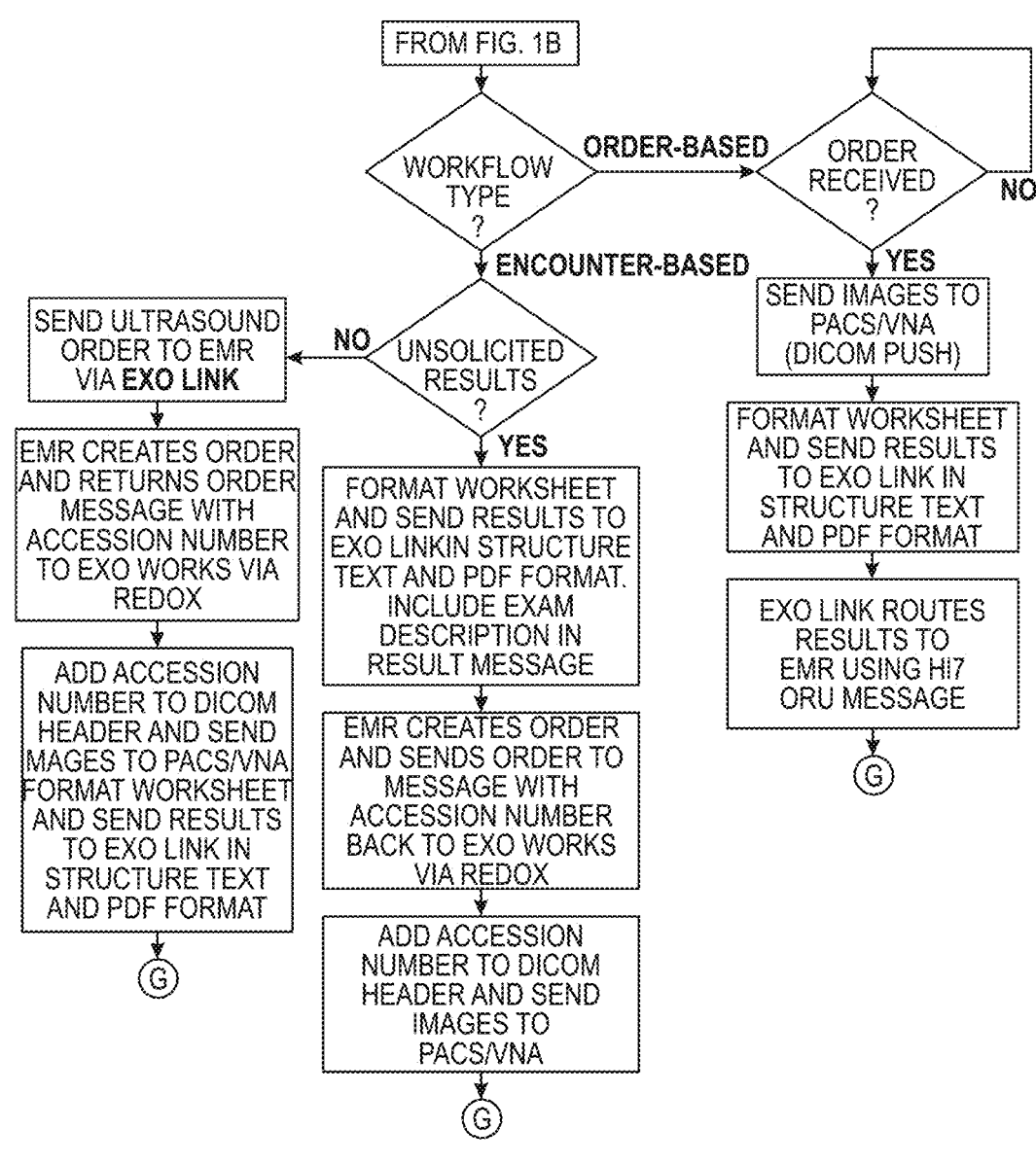
Figure 1D:
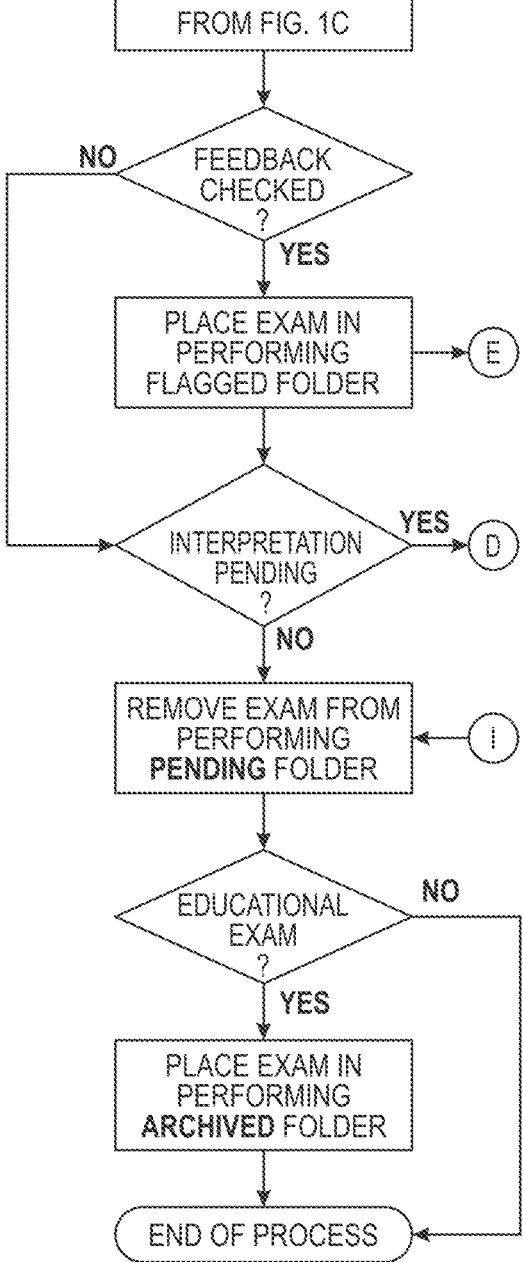

In some cases, the exam object can be routed to an Attending Inbox folder associated with an attending user assigned to the exam object is the check as to whether an attending user has been assigned to the exam object results in a value of "yes." In some cases, the exam object can be subjected to a check as to whether the exam object has an Exam State of "QA Pending" if the check as to whether an attending user has been assigned to the exam object results in a value of "no" (see, e.g., node "H" of FIG. 1B). If the check as to whether the exam object has an Exam State of "QA Pending" returns a value of "yes," platform, system, or method (e.g., server application thereof) may proceed with one or more steps of a QA Process (e.g., as shown in FIG. 1C and FIG. 1D). If the check as to whether the exam object has an Exam State of "QA Pending" returns a value of "no", the server application may end a process involving analysis, processing, and/or routing of the exam object, e.g., as shown in FIG. 1B.

As described above, an exam object may be subjected to a check as to whether a performing user assigned, identified, or associated with the exam object is credentialed for the exam (e.g., after an Educational Exam check of the exam object has returned a value or "no" and/or after a type value of the exam object is determined to be "clinical"), for instance, as shown in FIG. 1B. If the value of this Credential check is "yes," an Exam State of the exam object can be changed or updated to "Interpreted," in some embodiments.

In some cases, an exam object having an Exam State of "Interpreted" can be subjected to one or more archiving step (e.g., as shown in node "G" of FIG. 1B), for instance, wherein the exam object is stored in a data store, such as a database (e.g., an external medical record database). Following or in parallel with the one or more archiving step (e.g., which may comprise a plurality of consecutive attempts of the same archiving step), a server application can perform a check to determine via an Archiving check whether the one or more archiving step was successful.

For example, a server application can determine via an Archiving check whether archiving of the exam object (e.g., in a data store) is successful in a number of steps equal to or less than a predetermined value (e.g., 5 attempts, as shown in the example of FIG. 1B). If the value of the Archiving check is "yes" a server application can perform one or more of (i) changing or updating an Exam State of the exam object to "Archived," (ii) removing the exam object from the Performing Inbox folder and/or the Attending Inbox folder, (iii) routing the exam object or a portion of the information contained therein to a "Billed" folder, and/or (iv) routing the exam object to one or both of a "Performing Archived" folder and/or an "Attending Archived" folder.

In some cases, the exam object can be subjected to a check to determine whether the exam object is marked as (e.g., has an Exam State value that includes) "QA Pending". If the exam object is determined not to have a "QA Pending" value at this stage, a platform, system, or method described herein may end a process of evaluation, processing, or routing of the exam object (e.g., as shown in FIG. 1B). If the exam object is determined to have a "QA Pending" value at this stage, the exam object may be subjected to one or more steps of a QA review process (e.g., as shown following node "A" of FIG. 1B and FIG. 1C and FIG. 1D).

Alternatively, if the value of the Archiving check is "no" (e.g., wherein it is determined that archiving of the exam object was not successful after a number of attempts greater than or equal to a pre-determined threshold value), a server application can change or update an Exam State of the exam object to "Failed Archived" and/or route the exam object to (e.g., place the exam object in) one or more folders associated with one or more administrator users (e.g., one or more "Clinical Admin Flagged" folders associated with one or more individuals having an Clinical Administrator user role and/or one or more "IT Admin Inbox" folders associated with one or more individuals having an Information Technology (IT) Administrator user role).

In some cases, an exam object with an Exam State of "Failed Archived" can subsequently be subjected to a check to determine whether the exam object is marked as (e.g., has an Exam State value that includes) "QA Pending". The exam object can subsequently be subjected to one or more QA review process steps (e.g., if the QA Pending check returns a value of "yes") or a server application can end a process of evaluation, processing, or routing of the exam object (e.g., if the QA Pending check returns a value of "no").

As described above, server application can route an exam object to an Attending Inbox folder (e.g., if a performing user is not credentialed for analysis, interpretation, and/or approval of a "clinical" or non-educational exam object or if an attending user has been assigned to an exam object that is identified as non-clinical or "educational"), for instance, as shown in FIG. 1B.

In some cases, an authorized individual (e.g., an attending user assigned to the exam object) can perform one or more tasks with respect to the exam object, which can include analysis, interpretation, and/or approval of the exam object (e.g., as shown at node "D" of FIG. 1B). In some cases, an attending user can add or modify an Exam State of the exam object to "QA Pending" as part of the one or more tasks performed by the attending user with respect to the exam object.

In some cases, a server application can perform a check on the exam object to determine whether the exam object comprises an authorized signature of an attending user assigned to the exam object (e.g., after the exam object is placed in the Attending Inbox folder). If the check for the authorized signature returns a value of "no", the server application may perform the check again (e.g., after a pre-determined period of time or following a prompt from the assigned attending user). If the check for the authorized signature returns a value of "yes", the server application can perform a check to determine whether the Exam State is "educational" or has been changed to "educational" by the attending user.

In some cases, a server application can change an Exam State of the exam object to "Interpreted" if the Exam State is "educational" or has been changed to "educational". Additionally or alternatively, a server application can route the exam object to an Attending Archived folder associated with the assigned attending user and/or remove the exam object from the Attending Inbox folder if the Exam State is determined to be "educational" at Exam State check following confirmation of an authorized attending user signature. An exam object having an Exam State of "Interpreted" in addition to or subsequent to having an Exam State of "educational" can be subjected to a check by the server application to determine whether the exam object has an Exam State of "QA Pending". If the check returns a value indicating that the exam object has an Exam State of "QA Pending," the exam object can be subjected to one or more steps of a QA Process review (e.g., as shown subsequent to node "A" in FIG. 1C and FIG. 1D). If the check returns a value indicating that the exam object does not have an Exam State of "QA Pending," the exam object can be removed from the "Performing Pending" folder (e.g., subsequent to node "I", as shown in FIG. 1B and FIG. 1D). If, however, an exam object having an authorized signature of an attending user is determined not to have an Exam State of "educational" (or for which an Exam State has not been changed to "educational), a server application can perform one or more of the following (e.g., before performing a Workflow Type check): (i) set an Exam State of the exam object to "Interpreted", (ii) remove the exam object from the Attending Inbox folder, (iii) route the exam object to an "Attending Pending" folder, and/or (iv) perform an archiving step on the exam object (e.g., by routing the exam object to a data store, e.g., to be permanently or temporarily archived).

As described above, a server application can perform a Workflow Type check with respect to an exam object (e.g., after it has been determined that the exam object has an authorized signature of an attending user and that the exam object does not comprise an Exam State of "educational"), for example, as shown in FIG. 1C.

In some cases, a Workflow Type check performed with respect to an exam object can return a value of "Order-based". In some cases, a Workflow Type check performed with respect to an exam object can return a value of "Encounter-based". If a Workflow Type check performed by a server application with respect to an exam object returns a value of "Order-based," a server application can perform an "Order Received" check with respect to the exam object.

In some cases, an "Order Received" check can be used to determine whether an order has been received by the system for an (e.g., "clinical") exam object and/or for an analysis and/or an interpretation thereof.

In some cases, a server application can interrogate a data store (e.g., a folder comprising exam object orders received by the platform or system) for an exam object order identifying the exam object for which the "Order Received" check is being performed, during an "Order Received" check. A value of "no" returned from an "Order Received" check (e.g., which may result if a platform or system described herein is not able to detect a record of an order for the exam object) can cause the "Order Received" check to be repeated (e.g., at a predetermined interval from the prior "Order Received" check or upon a prompt from a user, for example until a value of "yes" is returned). If a value of "yes" is returned during an "Order Received" check, a server application can route (e.g., send) all or a portion of the exam object (e.g., one or more images of the exam object) to a data store (e.g., a database, such as a Picture Archiving and Communications System (PACS) or Vendor Neutral Archive (VNA)), for example, via a DICOM push signal, which may be a signal used to send a Digital Imaging and Communications in Medicine (DICOM) formatted image file to a database or data store (e.g., for archiving of the one or more images).

In some cases, a client application or server application can format a worksheet of the exam object and/or route the exam object (or a portion thereof) to a value of "yes" returned during an "Order Received" check (e.g., after routing of one or more images of the exam object to a PACS or VNA) can route the exam object or portion thereof to a module of the server application.

In some cases, the client application or the server application can format the exam object or portion thereof (e.g., a worksheet of the exam object) in structure text and/or Portable Document Format (PDF) file format, e.g., prior to routing the exam object or portion thereof to the module of the server application. In some cases, a server application can route the exam object or portion thereof to a data store (e.g., an Electronic Medical Records (EMR) database), for example, for archiving of the exam object or portion thereof (e.g., as shown at node "G" of FIG. 1C). In some cases, the exam object can be routed (e.g., sent) by the server application to the data store (e.g., the EMR database) as a Health Level 7 (HL7) Observation Result (ORU) message.

As described above, a Workflow Type check can return a result of "encounter-based," which can cause the server application to lead to an "Unsolicited Results" check performed by the server application with respect to the exam object. In some cases, an "Unsolicited Results" check can comprise interrogating a data store (e.g., a data store comprising a folder wherein one or more orders (e.g., ultrasound exam orders) for exam object are stored).

In some cases, a server application can be used to route an ultrasound order to a data store, such as an EMR database, when a value of "no" is returned during the "Unsolicited Results" check. In some cases, an order comprising an Accession Number (e.g., created by the EMR database) can be received (e.g., from the EMR database) by the server application (e.g., via Redox). In some cases, a client application or a server application can be used to add the Accession Number of an order to an exam object or portion thereof (e.g., to a DICOM header of one or more images of an exam object).

In some cases, a server application can be used to route the exam object (e.g., comprising the added Accession Number) to a data store (e.g., a PACS or VNA database). In some cases, the server application can format the exam object or portion thereof (e.g., a worksheet of the exam object) in structure text format and/or Portable Document Format (PDF). In some cases, a server application can route the exam object or portion thereof to a data store (e.g., an Electronic Medical Records (EMR) database), for example, for archiving of the exam object or portion thereof (e.g., as shown at node "G" of FIG. 1C).

In some cases, archiving of an exam object or portion thereof (e.g., as shown at a node "G" of FIG. 1C) can comprise placing the exam object or portion thereof in a data store (e.g., a folder of a data store, such as an archived folder of a data store).

In some cases, a client application or server application can format a worksheet of the exam object and/or route the exam object (or a portion thereof) to a value of "yes" returned during an "Unsolicited Results" check (e.g., after routing of one or more images of the exam object to a PACS or VNA) can route the exam object or portion thereof to a module of the server application.

In some cases, the client application or the server application can format the exam object or portion thereof (e.g., a worksheet of the exam object) in structure text and/or Portable Document Format (PDF) file format, e.g., prior to routing the exam object or portion thereof to the module of the server application. In some cases, the client application or server application can be used to modify the exam object (e.g., a result message of the exam object) to include an Exam description (for example, comprising information input by a user, e.g., via a client application).

In some cases, a client application or a server application can be used to add the Accession Number of an order to an exam object or portion thereof (e.g., to a DICOM header of one or more images of an exam object). In some cases, a server application can be used to route the exam object (e.g., comprising the added Accession Number) to a data store (e.g., a PACS or VNA database), for example, for archiving of the exam object or portion thereof (e.g., as shown at node "G" of FIG. 1C).

QA Routing and QA Processes

In some cases, a platform, system, or method described herein can comprise one or more steps of a QA Process (e.g., a QA Review Process), for example, as shown in FIG. 1C and/or FIG. 1D. In some cases, a QA Process or portion thereof can be initiated after an exam object has been marked as "QA Pending" (e.g., wherein an Exam State of the exam object is or has been modified to be "QA Pending") and/or when the exam object has been routed (e.g., via a server application) to one or more "QA Reviewer Inbox" folder, for example, as shown in FIG. 1A and/or FIG. 1B (e.g., at a node "A").

In some cases, an individual assigned a user role of "QA Reviewer" (e.g., a "QA Reviewer user") can access the exam object (e.g., via a client application) in the QA Reviewer Inbox folder (e.g., for review of one or more images of the exam object and/or an Exam report of the exam object, which may be comprised in a worksheet of the exam object).

In some cases, a QA Reviewer user can modify a portion of the exam object (e.g., a worksheet of the exam object or portion thereof, such as a QA Worksheet of the exam object), for example using a client application, to include information, which may comprise an exam grade, feedback (e.g., QA feedback, which may pertain to an analysis or interpretation of the exam object or portion thereof, for instance, which was provided by a performing user and/or an attending user), an indication as to whether the exam object and/or analysis or interpretation associated therewith is acceptable (e.g., by marking (e.g., checking) a field indicating that the exam is acceptable), an indication as to whether review of the feedback is requested or required, for instance of by a performing user (e.g., by marking (e.g., checking) a field (e.g., a "Review Feedback" field) in a user interface of the client application or server application), and/or an authorized signature (e.g., authorized electronic signature) of the QA Reviewer user.

In some cases, an Exam State of an exam object can be added, changed, or updated to reflect "QA Reviewed" status, for instance after a QA Reviewer user has reviewed the exam object or portion thereof or after the QA Reviewer has modified the exam object to include information e.g., as shown in FIG. 1C.

In some cases, a server application can perform a "Feedback Checked?" check after the QA Reviewer user has reviewed the exam object (e.g., as shown in FIG. 1D). In some cases (e.g., wherein a QA Reviewer user has indicated in the exam object that the QA feedback should be reviewed, for instance by marking a corresponding field of the exam object, which can result in a "Feedback Checked" check returning a value of "yes"), a server application can route the exam object to a "Flagged" folder (e.g., of a data store).

In some cases, routing of an exam object to a "Flagged" folder (e.g., placing the exam object in a "Flagged" folder) can initiate one or more steps of a "Review QA Feedback Process," for instance as shown at node "E" of FIG. 1C and FIG. 1D. In some cases (e.g., wherein a QA Reviewer user has not indicated in the exam object that the QA feedback must be or should be reviewed, for instance by leaving a corresponding field of the exam object unmarked, which can result in a "Feedback Checked" check returning a value of "no"), a server application can perform an "Interpretation Pending" check.

In some cases, a "yes" result of an "Interpretation Pending" check (e.g., during a QA Review Process, for instance as shown in FIG. 1D) can lead to an attending user performing an interpretation of information (e.g., comprising analysis of one or more images of the exam object) provided by a performing user, for instance, by routing the exam object to an Attending Inbox folder and/or updating an Exam State of the exam object to "Complete." In some cases, a "no" result of an "Interpretation Pending" check (e.g., during a QA Review Process, for instance as shown in FIG. 1D) can result in a server application removing the exam object from a "Performing Pending" folder. As shown in FIG. 1D, a "no" result from an "Exam Status QA Pending" check (e.g., as shown at node "I" of FIG. 1A) can result in the exam object being removed from the "Performing Pending" folder (e.g., as shown in node "I" of FIG. 1D).

In some cases, a server application can perform an "Educational Exam" check after the exam object is removed from the "Performing Pending" folder, e.g., as shown in FIG. 1D. In some cases, a "no" result from the "Educational Exam" check can result in an end of a QA Process and/or of an instance or implementation of a process of a platform, system, or method described herein.

In some cases, a "yes" result from the "Educational Exam" check can result in the exam object being routed to (e.g., placed in) an "Archived" folder (e.g., of a data store), for instance, by the server application. In some cases, placing an exam object in an "Archived" folder (e.g., as shown in FIG. 1D) can result in an end of a QA Process and/or of an instance or implementation of a process of a platform, system, or method described herein.

In some cases, a QA Process can be initiated (e.g., by marking the exam object as "QA Pending" or by placing the exam object in a "QA Reviewer Inbox") by a system or platform described herein or a portion thereof (e.g., a server application or module thereof or a client application or a module thereof).

In some cases, initiation of a QA Process by a system or platform described herein or a portion thereof can be based on a (e.g., predetermined) a selection process mediated by the system, platform, or method (e.g., a selection process based on a predetermined statistical probability of selection for QA review of an exam object). In some cases, a selection process for initiating a QA Process review of an exam object (e.g., mediated by a system or platform described herein) can be based on one or more of a facility (e.g., a medical school facility, urgent care facility, or private practice facility), a specialty (e.g., "Adult Critical Care" ("CCU"), "Adult Intensive Care" ("ICU"), "Anesthesia", "Emergency Medicine," "MSK," "Obstetrics," "Pediatric Critical Care" ("PCCU"), "Pediatric Intensive Care" ("PICU"), or "Surgery"), for example, wherein a probability of selection is associated with one or more of the listed specialties), and/or a user group (e.g., a user designation of the performing user, which may include "student" or "medical student," "resident," "fellow," "attending," "nurse," "registered nurse" ("RN"), and/or "physician's assistant" ("PA")).

For example, a rate of selection for exam objects entering a QA Process after review and/or analysis by a performing user can be based on the performing user's type (e.g., wherein exam objects are selected for QA Process review by the platform, system, or method at a rate of 100% for "student" performing users, 100% for "resident" performing users, 50% for "fellow" performing users, 10% for "attending" performing users (or "attending" attending users), and/or 10% for "PA" performing users). In some cases, initiation of a QA Process can be mediated manually by one or more users of the system, platform, or method.

Review QA Feedback Processes and Routing

An instance or implementation of a platform, system, or method described herein can comprise performing one or more steps of a QA Feedback Process, e.g., as shown in FIG. 1C. In some cases, review of feedback provided by a QA Reviewer user (e.g., in an exam object), for example, as part of a Review QA Feedback Process, such as the process shown in FIG. 1C, can be suggested or required of another user (e.g., a performing user and/or an attending user). In some cases, one or more steps of a Review QA Feedback Process can be initialized by an exam object being placed in a "Flagged" folder (e.g., as shown in FIG. 1D) and/or by an exam object being modified by a QA Reviewer user such that a "Review Feedback" field is marked.

In some cases, a Review QA Feedback Process can comprise a Performing User logging into a client application, the Performing User selecting the "Flagged" folder (e.g., in which the exam object is stored), the Performing User opening the exam object, and/or the Performing User reviewing information (e.g., QA feedback) provided by the QA Reviewer User.

In some cases, a server application can remove the exam object from the "Flagged" folder (e.g., a "Performing Flagged" folder) when one or more tasks selected from the Performing User opening the exam object from the "Flagged" folder, the information (e.g., comprising QA Feedback) provided by the QA Reviewer User being selected or opened (e.g., wherein the information is located in a QA worksheet of the exam object), and/or an authorized signature or marked field is provided by the Performing User, e.g., in the QA worksheet of the exam object. In some cases, a Review QA Feedback Process can be ended after the exam object is removed from the "Flagged" folder, for instance, as shown in FIG. 1C.

Clinical Administrative Escalation Processes and Routing

In some cases, an instance or implementation of a platform, system, or method described herein can comprise performing one or more steps of a Clinical Administrative ("Clinical Admin") Escalation Process, e.g., as shown in FIG. 1C. In some cases, a Clinical Admin Escalation Process or portion thereof can be initiated after an exam object is routed to a "Flagged" folder (e.g., as shown in FIG. 1D, for instance, as part of a QA Process). A Clinical Admin Escalation Process can comprise an individual assigned a Clinical Admin user role (e.g., a "Clinical Admin" user) logging into the server application, selecting a "Flagged" folder (e.g., a "Clinical Admin Flagged" folder) comprising an exam object for review, and/or the Clinical Admin user reviewing one or more exam objects flagged for review (e.g., each exam object flagged for review) by the system or by a QA Reviewer user.

In some cases, a Clinical Admin Escalation Process can comprise a server application notifying (e.g., via email or mobile device text messaging) one or more performing user and/or one or more attending user associated with the exam object of a task pending completion (e.g., a task that the performing user(s) and/or attending user(s) are requested or required to perform). The server application can perform a "Flag Removed" check, which can comprise determining whether one or more conditions creating a "Flag" or "Flagged" Exam State of the exam object (e.g., as indicated or input by a QA Reviewer user) has been satisfied or removed.

In some cases, the one or more conditions can comprise reviewing feedback provided by a QA Reviewer user and/or archiving of all or a portion of the exam object. In some cases, a server application can remove an exam object from the "Flagged" folder and/or remove a "Flag" or a "Flagged" Exam State from the exam object when a "Flag Removed" check returns a value of "yes." In some cases, the "Flag Removed" check can be repeated if the "Flag Removed" check returns a value of "no" (e.g., until the "Flag Removed" check returns a value of "yes"). In some cases, a Clinical Admin Escalation Process can be ended after an exam object is removed from the "Flagged" folder, for instance, as shown in FIG. 1C.

Turning to FIG. 2A, addition, removal, or modification of a patient demographics information (e.g., in an EMR record for the patient) can affect performance of a server application or client application. For instance, a change in a patient demographics information (e.g., a change in the patient's status as registered, transferred, discharged, or updated) can result in a server application of a platform, system, or method being received via HL7 notification.

In some cases, a server application or client application of the system, platform, or method can add, update, delete, or transfer all or a portion of patient data (e.g., patient demographic information) to an individual having an appropriate user role (e.g., an individual having a user role ("Specialty") relevant to the change in patient demographic information), for instance, as shown in FIG. 2A.

Turning to FIG. 2B, an ultrasound examination order (e.g., placed via an EMR) can be received by a server application of a platform, system, or method described herein. In some cases, the server application can route the examination order (e.g., "ultrasound examination order", "U/S exam order", or "U/S order") to a client application.

In some cases, the server application and/or the client application can add, update, delete or transfer the examination order to an individual having an appropriate user role (e.g., an individual having a user role ("Specialty") relevant to the change in patient demographic information), for instance, as shown in FIG. 2B.

Figures 4A, 4B:
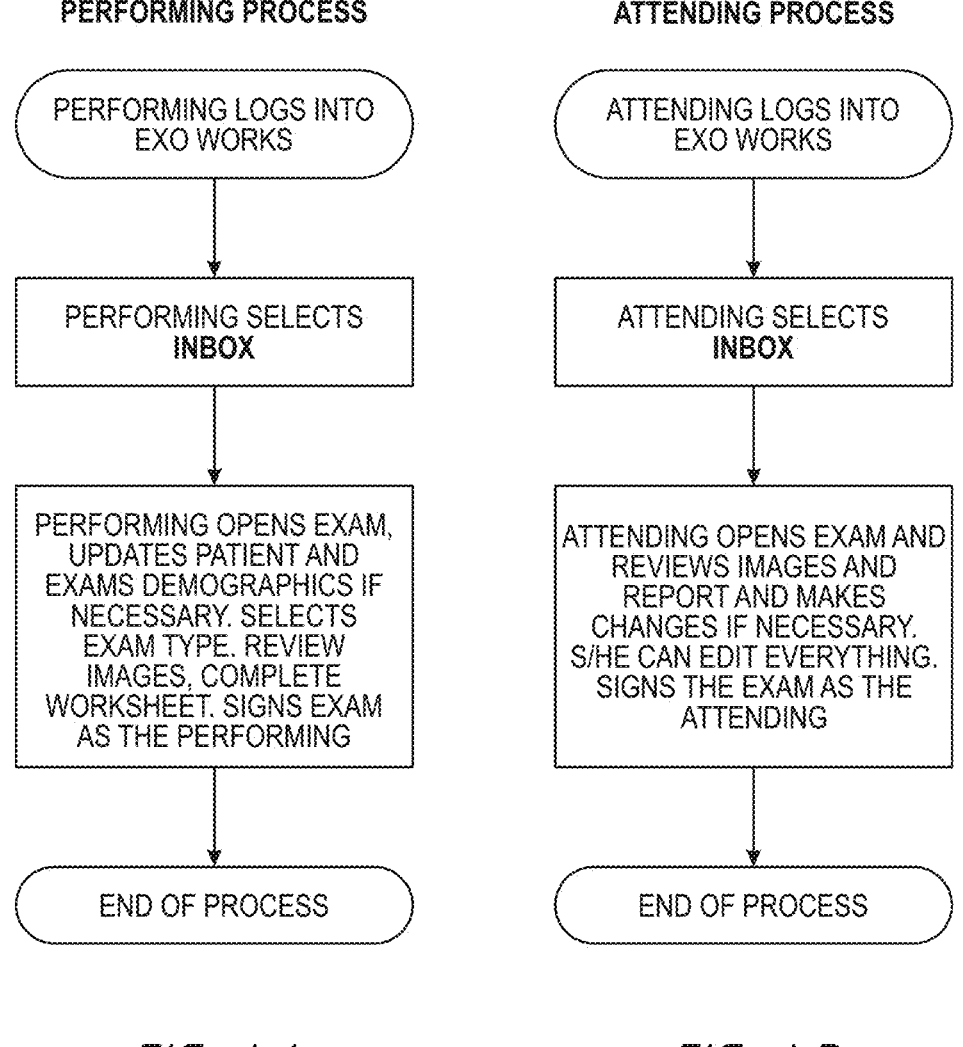
FIG. 4A shows a non-limiting example of a process comprising review and analysis of an examination object by a performing user, in accordance with some embodiments.
FIG. 4B shows a non-limiting example of a process comprising review of an examination object by an attending user, in accordance with some embodiments.

Turning to FIG. 4A, a platform, system, or method described herein can comprise a Performing Process. In some cases, a Performing Process can comprise a performing user logging into a client application. In some cases, a Performing Process can comprise the performing user selecting an inbox folder (e.g., a "Performing Inbox" folder). In some cases, a Performing Process can comprise opening an exam object, updating one or more patient demographic information data of the exam object. In some cases, a Performing Process can comprise the performing user selecting an exam type, which can cause the client application to display and/or access one or more exam objects having the selected exam type.

In some cases, a performing user can review one or more images of one or more exam objects and/or partially or fully complete one or more worksheets of the one or more exam objects. In some cases, a Performing Process can comprise the performing user providing an authorized signature as the performing user. In some cases, a Performing Process can end after an authorized signature is provided on the exam object by the performing user.

Turning to FIG. 4B, a platform, system, or method described herein can comprise an Attending Process. In some cases, an Attending Process can comprise an attending user logging in to a client application. In some cases, an Attending Process can comprise the attending user selecting an inbox folder (e.g., a "Attending Inbox" folder). In some cases, an Attending Process can comprise opening an exam object, changing (e.g., updating) data of the exam object. In some cases, an Attending Process can comprise the performing user selecting an exam type, which can cause the client application to display and/or access one or more exam objects having the selected exam type.

In some cases, an attending user can review one or more images of one or more exam objects and/or partially or fully complete one or more worksheets of the one or more exam objects. In some cases, an attending user can be able to add or edit one or more aspects (e.g., analysis provided by a performing user, interpretations of the analysis provided by the performing user, and/or an Exam State) of the exam object.

In some cases, an Attending Process can comprise the attending user providing an authorized signature as the attending user. In some cases, an Attending Process can end after an authorized signature is provided on the exam object by the attending user.

Encounter-Based and Order-Based Modes

Figures 5A, 5B:
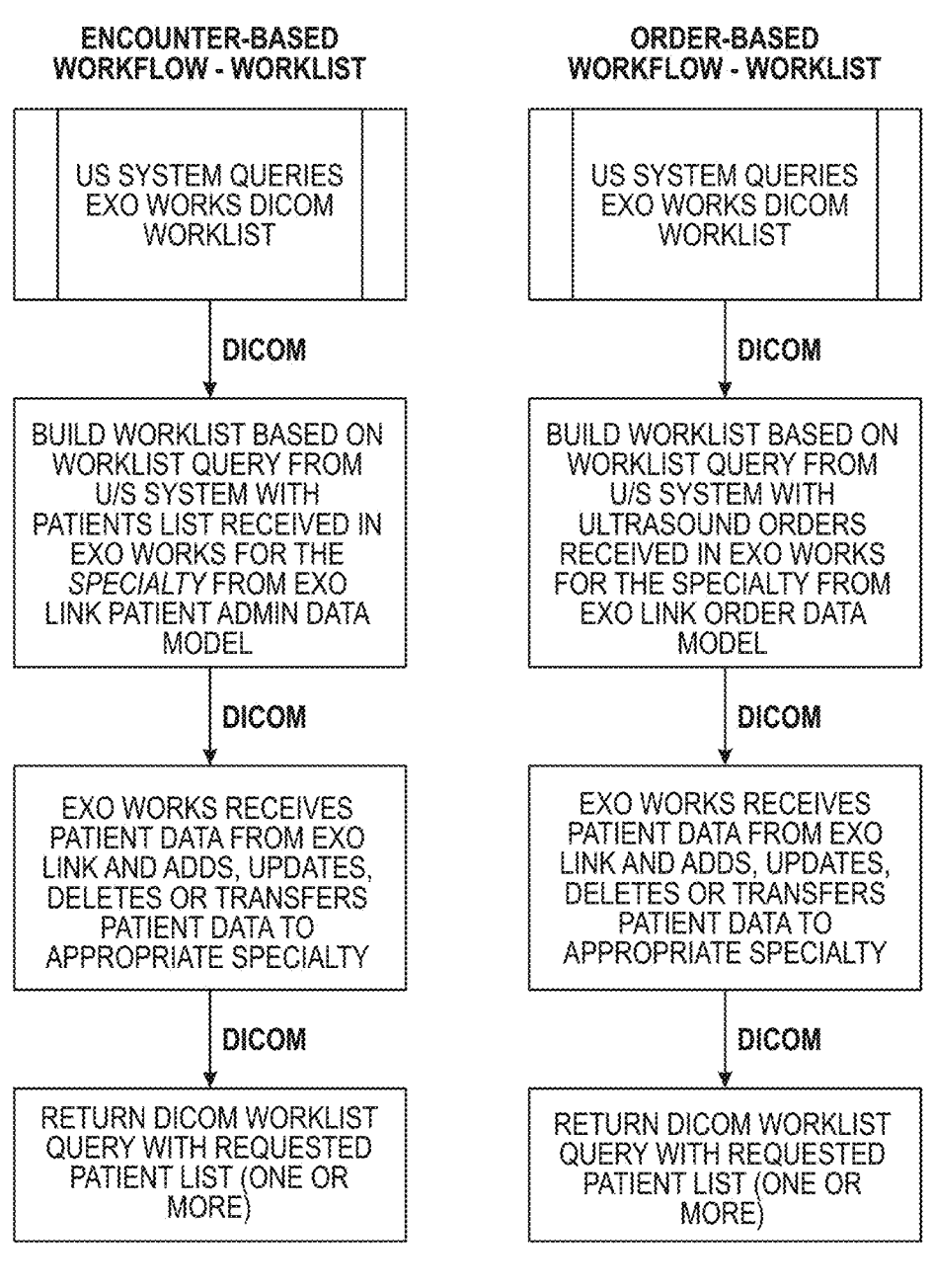
FIG. 5A shows a non-limiting example of a process comprising encounter-based examination object routing and processing, in accordance with some embodiments.
FIG. 5B shows a non-limiting example of a process comprising order-based examination object routing and processing, in accordance with some embodiments.

Turning to FIG. 5A and FIG. 5B, a platform or system described herein can be configured to perform point-of-care examination (e.g., comprising routing, processing, and/or analysis of one or more exam objects) in one or more modes (e.g., a plurality of modes). For instance, a platform or system described herein may be capable of performing point-of-care examination (e.g., comprising routing, processing, and/or analysis of one or more exam objects) in an "encounter-based" mode and/or in an "order-based" mode, e.g., as described herein.

In some cases, the ability of a single system or platform to process point-of-care examination requests or tasks in multiple modalities can increase the flexibility and robustness of the system or platform, which can be advantageous in situations wherein the entity or entities operating the system or platform face the possibility of heterogeneous examination intake circumstances.

For example, new examination events (e.g., comprising one or more exam objects received by the platform or system, which may be able to use an "order-based" examination mode) can be pre-planned (e.g., scheduled examinations) or not pre-planned (e.g., examinations associated with acute care or emergency patient care, which may require an "encounter-based" examination mode). The circumstances of the examination event intake can affect which data relevant or necessary to the routing, processing, or analysis of an exam object are available at the time of intake (e.g., receipt of the exam object by a server application or client application). For instance, a platform or system configured to facilitate processes involving point-of-care examination in an "order-based" examination type (e.g., wherein the exam object may include or be accompanied by some, most, or all of the data relevant to or required for routing, processing, and/or analysis of the exam object, for instance, where the production, modification, routing, processing, or analysis of the exam object is scheduled or is non-urgent and/or wherein the exam object order may be placed by a provider, such as a performing user or an attending user prior to or in parallel with the point-of-care examination process of the platform or system to obtain the relevant or required data) may benefit from process streamlining (e.g., by using provided medical record data provided with the exam object and/or request, such as patient-demographics, rather than querying an outside database for the same information), e.g., compared to a system that is not capable of or configured for "order-based" examination.

In some cases, a platform or system configured to facilitate processes involving point-of-care examination of an "encounter-based" examination type (e.g., wherein the exam object may not include at least some data relevant to or required for routing, processing, and/or analysis of the exam object) may benefit from system or platform features that allow for acquisition and/or incorporation of the relevant or required information into the exam object and/or a process comprising routing, processing, and/or analysis of the exam object using the platform or system.

In accordance with some embodiments, a platform or system capable of employing an "encounter-based" mode (e.g., which may include an "encounter-based" process or workflow) may be advantageous in situations (e.g., emergency or urgent care situations) where data relevant to or required for routing, processing, or analysis of the exam object is not available at the time of creation or receipt of the exam object (e.g., wherein an exam object comprises incomplete patient medical record data (e.g., patient demographic information) at the time of receipt) by a server application or client application of the system or platform.

In such cases, the ability of a system or platform described herein to operate in an "encounter-based" mode can reduce the burden on users to gather and/or provide the relevant or required data to the server application or client application, e.g., leveraging the system or platform's ability to gather and/or incorporate such data from sources such as outside databases, such as an EMR database, for instance to request an exam object order (e.g., in parallel with actions performed by one or more users, such as performing users and/or attending users, on the exam object(s)).

In some cases, a system, platform, or method configuration (e.g., workflow type) can comprise selecting a facility (e.g., location of examination, exam object analysis, or exam object interpretation), selecting a specialty (e.g., a medical specialty relevant to the examination and/or to a performing user or attending user), selecting the workflow type (e.g., "encounter-based" or "order-based", and/or saving input settings.

In some cases, a platform or system described herein can be configured to perform point-of-care examination (e.g., comprising routing, processing, and/or analysis of one or more exam objects) in an "Encounter-based" mode (e.g., an "Encounter-based" workflow type). In some cases, a platform or system configured to perform point-of-care examination in an "encounter-based" mode can comprise one or more steps shown in FIG. 5A.

For example, a platform, system, or method comprising an "encounter-based" mode can comprise (e.g., be initiated by) an ultrasound imaging system querying a (e.g., DICOM-formatted) worklist of a client application (e.g., "Exo Works") interfaced with a server application (e.g., "Exo Link"). In some cases, an "encounter-based" mode can comprise building a worklist based on the worklist query from the ultrasound imaging system (e.g., "U/S System"), for instance using a list of patients (e.g., specific to a clinical specialty relevant to the clinical field of the worklist query and/or exam object) received from the server application or a module thereof (e.g., "Exo Link Patient Admin" data model).

In some cases, the client application can receive patient data from the server application and can be used to add, update, delete, or transfer data (e.g., patient data) to one or more users, user roles, or data stores of an appropriate specialty (e.g., via the server application). In some cases, an "encounter-based" mode can comprise returning the DICOM worklist query with the requested list of one or more patients matching the request criteria.

In some cases, a platform or system described herein can be configured to perform point-of-care examination (e.g., comprising routing, processing, and/or analysis of one or more exam objects) in an "Order-based" mode (e.g., an "Order-based" workflow type). In some cases, a platform or system configured to perform point-of-care examination in an "order-based" mode can comprise one or more steps shown in FIG. 5B.

For example, a platform, system, or method comprising an "order-based" mode can comprise (e.g., be initiated by) an ultrasound imaging system ("U/S System") querying a (e.g., DICOM-formatted) worklist of a client application (e.g., "Exo Works") interfaced with a server application (e.g., "Exo Link"). In some cases, an "order-based" mode can comprise building a worklist based on a worklist query from the ultrasound imaging system, for instance using ultrasound orders received by the client application from the server application or a module thereof (e.g., "Exo Link Order" data model).

In some cases, the client application can receive patient data from the server application and can be used to add, update, delete, or transfer data (e.g., patient data) to one or more users, user roles, or data stores of an appropriate specialty (e.g., having a specialty value matching the associated role or query). In some cases, an "order-based" mode can comprise returning the DICOM worklist query with the one or more ultrasound orders (e.g., exam objects) matching the request criteria.

Interfaces and Insights

Figure 6:
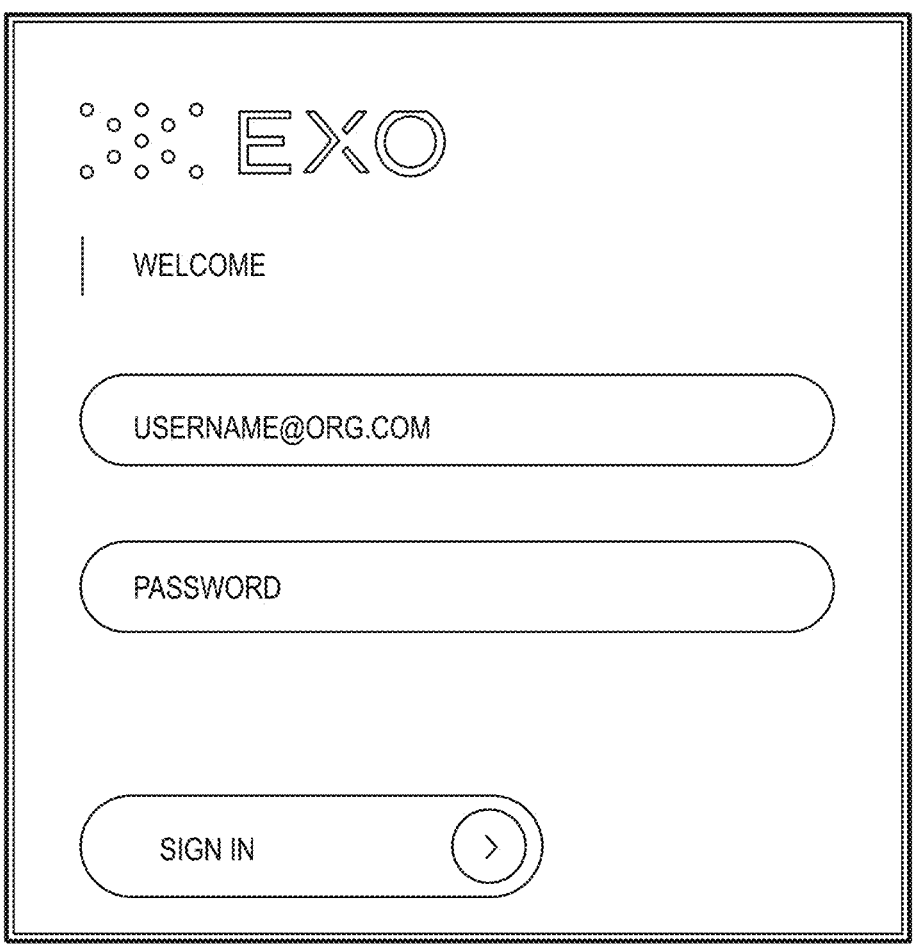
FIG. 6 shows a non-limiting example of a log-in screen of a client application, in accordance with some embodiments.

A client application can comprise or present a user with a log in screen (e.g., as shown in FIG. 6), for example, when the user opens the client application. In some cases, a log in screen of a client application or server application can comprise username, email, and/or password input fields.

In some cases, a log in screen can comprise a "Sign In" button. In some cases, a system, platform, or method can prompt a user to agree or decline a privacy policy and/or a terms of use policy. In some cases, providing valid login information and/or acceptance of a privacy policy or terms of use policy at the log in screen can cause the system, platform, or method to present the user with a dashboard screen, which can comprise the user's inbox and/or an Exam Folder Menu (e.g., as shown in FIG. 8).

Figure 7:
FIG. 7 shows a non-limiting example of an Organization Code screen of a client application, in accordance with some embodiments.

Turning to FIG. 7, a client application can comprise or present a user with an Organization Code Prompt screen (e.g., "Org Code Screen"), for example, when a user opens the client application on a mobile device. In some cases, an Org Code Screen can comprise a field for a user to enter an organization code ("Org Code"). In some cases, an Org Code Screen can comprise a "Validate" button. In some cases, entry of a valid organization code at the Org Code Screen can cause the client application to present the user with a log in screen (e.g., as shown in FIG. 6).

Figure 8:
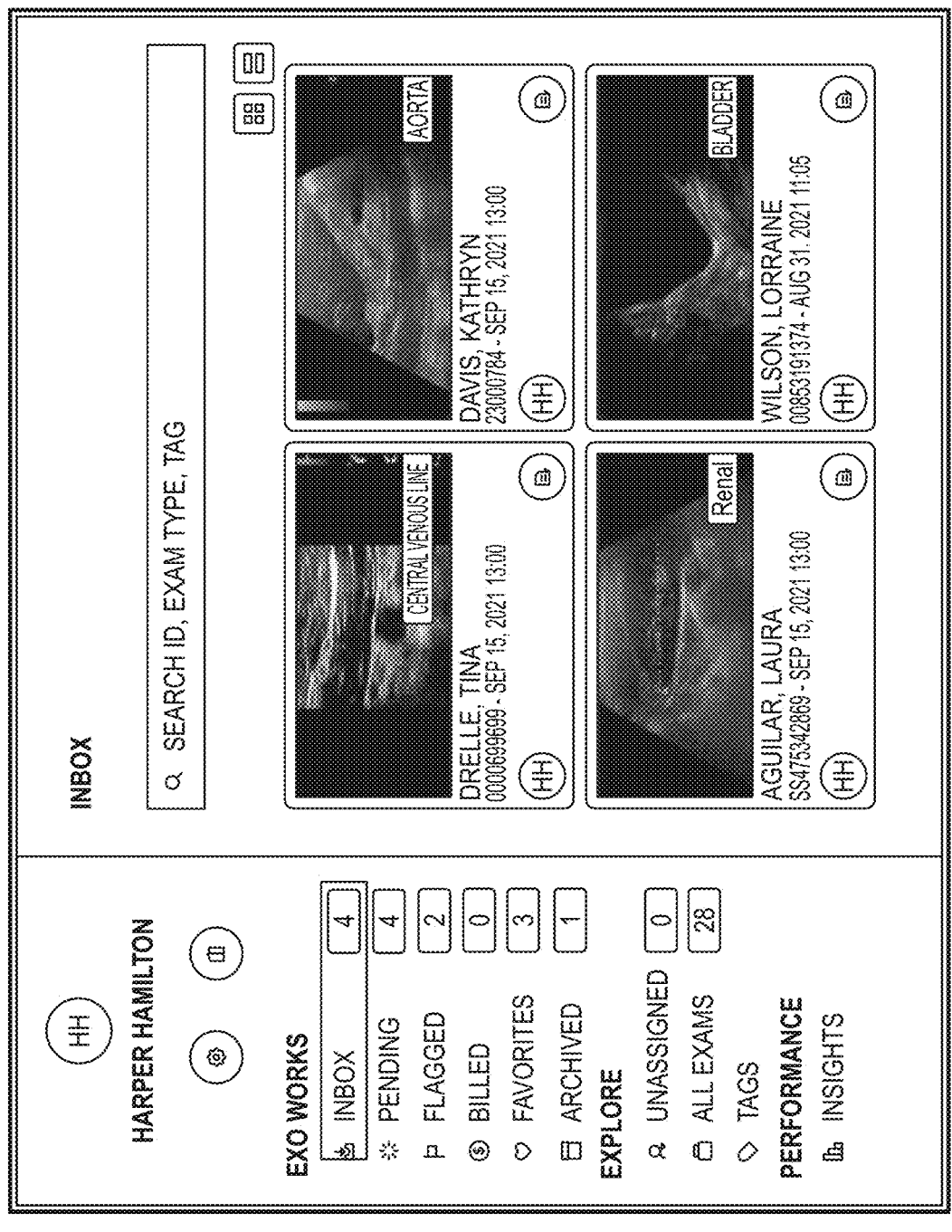
FIG. 8 shows a non-limiting example of an Exam Folder Menu screen of a client application, in accordance with some embodiments.

Turning to FIG. 8, a platform, system, or method or client application thereof can comprise a user screen (e.g., an "Inbox" folder associated with one or more user roles), which can comprise an Exam Folder Menu. As shown in FIG. 8, a user screen can comprise text indicating the user's name, a settings button (e.g., leading to a settings menu), an Exam Folder Menu (e.g., comprising links to one or more of an inbox folder, a pending folder, a flagged folder, a billed folder, a favorites folder, an archived folder, an unassigned folder, an all exams folder, a tags menu, and an insights menu).

In some cases, a user screen can comprise a search bar (e.g., for searching text of exam objects within one or more folders). In some cases, a search bar of a user screen can be used to search one or more populations of stored exam objects by examination date, patient name, patient medical record number (MRN), provider name (e.g., name of clinical care provider), examination category (for example, "clinical" or "educational", e.g., as described herein), examination type (e.g., renal or cardiac exam type), accession number, and/or one or more search "tags" associated with the exam object(s).

Figure 9:
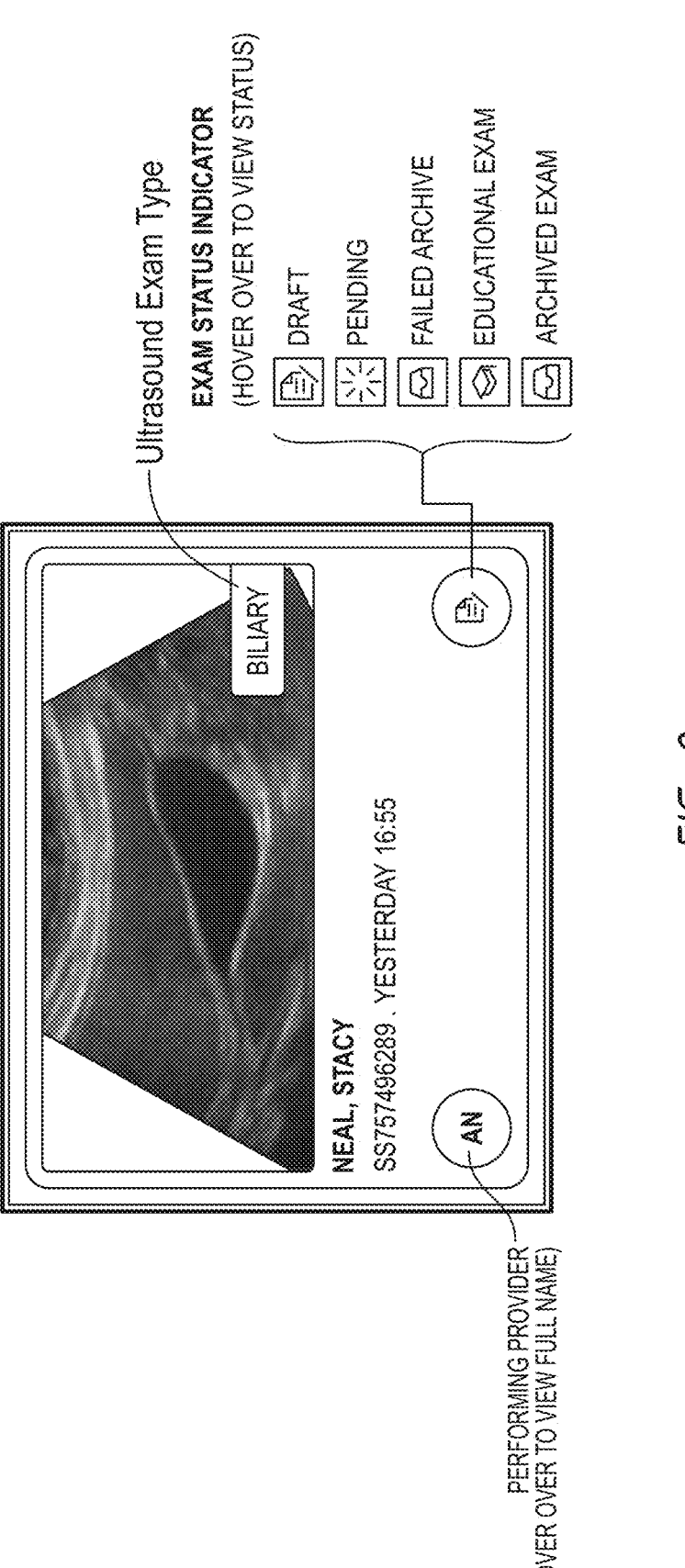
FIG. 9 shows a non-limiting example of an exam card of an Exam Folder Menu screen of a client application, in accordance with some embodiments.

In some cases, a user screen can comprise exam cards (e.g., one or more exam preview cards) or list entries for all or a portion of the exam objects in a selected folder. In some cases, an exam card or list entry can display a patient name, a patient ID number, an indication of a performing user's name (e.g., as shown in FIG. 9) a date and/or time of examination, an exam type (e.g., as identified in FIG. 9), and/or a button to access the exam status indicator button (e.g., wherein hovering over the button with a cursor can present the user with associated tags or Exam States, such as "Draft" (e.g., which can indicate that the performing provider has not yet provided his or her authorized signature to ("signed off on") the exam object), "Pending" (e.g., which can indicate that the exam object is waiting to be reviewed and/or interpreted by an attending provider and/or one or more QA reviewer), "Failed Archive" (e.g., which can indicate that an attempted transfer of the exam object to an EMR, PACS, or VNA data store has failed), "Educational" (e.g., which can indicate that the exam object is for educational or teaching purposes), or "Archived" (e.g., which can indicate that the exam object has been successfully transferred to an EMR, PACS, or VNA data store), for example, as shown in FIG. 9).

Figure 10:
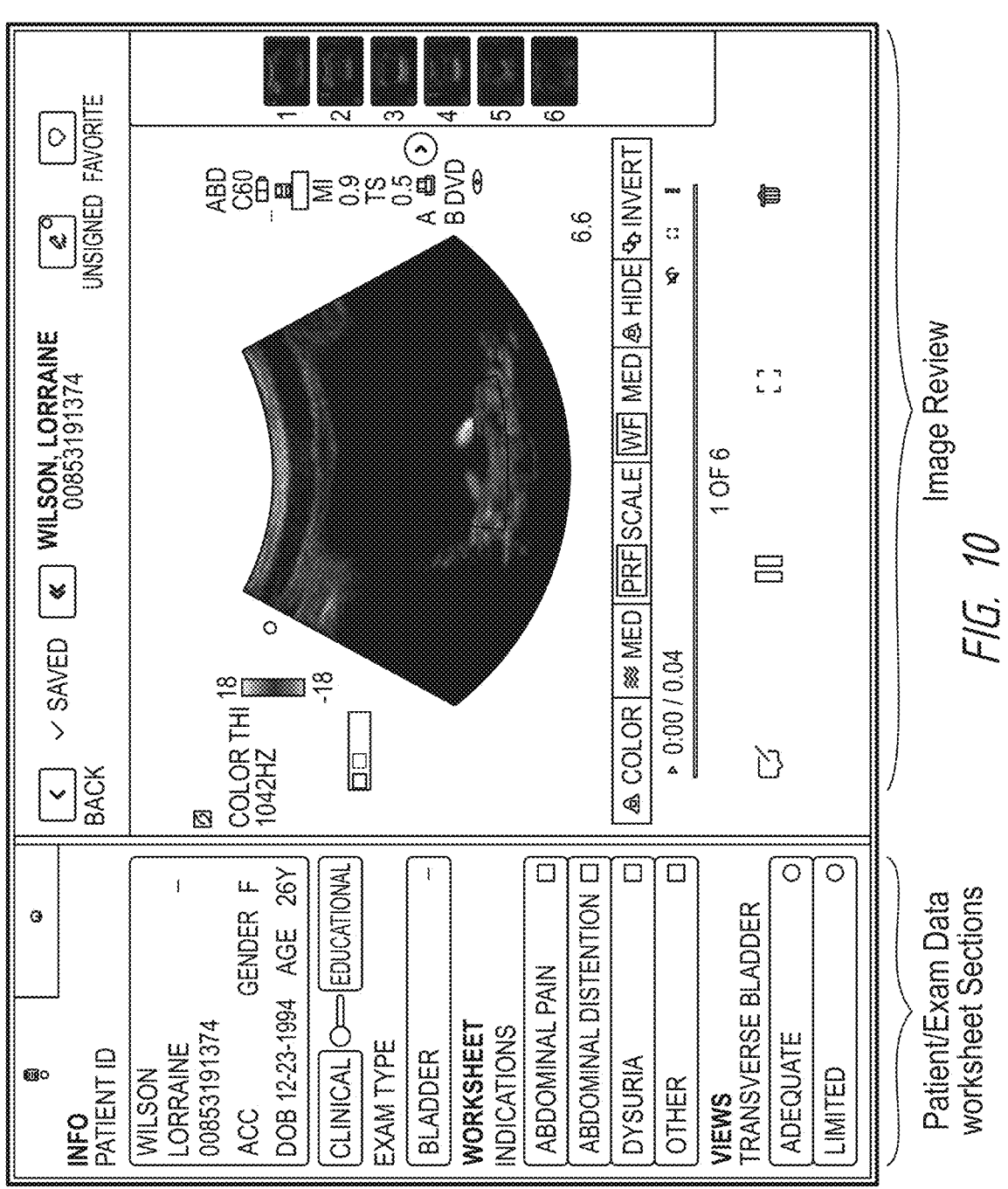
FIG. 10 shows a non-limiting example of an Exam Review Screen of a client application, in accordance with some embodiments.

In some cases, selecting from an Exam Folder Menu (e.g., a user screen) an exam card or list entry indicating an exam object can cause an Exam Review Screen (e.g., as shown in FIG. 10) to be accessed, loaded, and or displayed (e.g., by the client application). In some cases, an Exam Review Screen can comprise one or more Patient/Exam Data Worksheet Sections and/or an Image Review display (e.g., as shown in FIG. 10).

In some cases, an Exam Review Screen can be used to view one or more images (or image video clips) of an exam object, edit data associated with the exam object (e.g., patient information associated with the exam object and/or examination data associated with the exam object), and/or complete or review an examination worksheet, which may comprise performing a QA process review.

Figure 11:
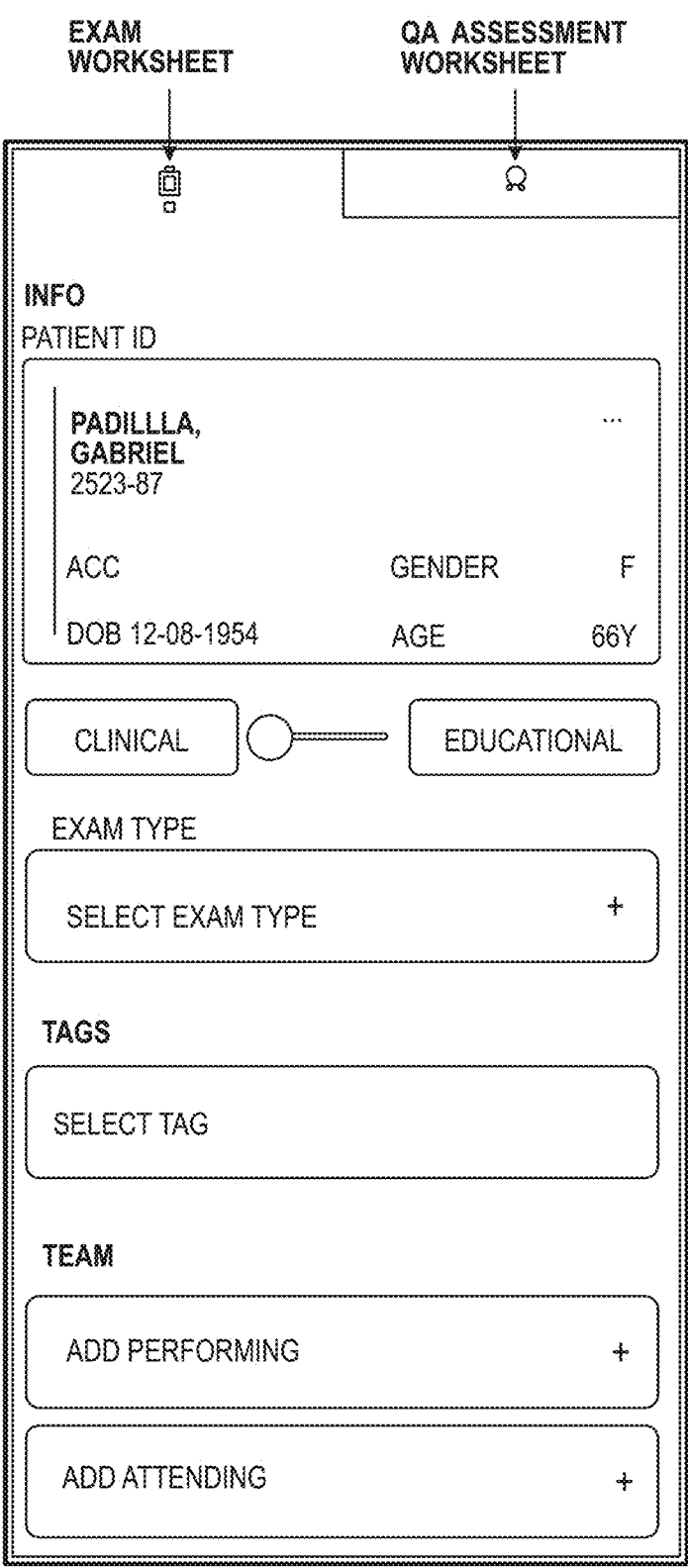
FIG. 11 shows a non-limiting example of an Exam Worksheet Section of an Exam Review Screen, in accordance with some embodiments.

As shown in FIG. 11, a client application may allow a user to select between a plurality of worksheets of the exam object, for instance, by selecting from a plurality of tabs (e.g., "Exam Worksheet" tab and "QA Assessment Worksheet", as shown in FIG. 11). A worksheet section (e.g., a Patient/Exam Data Worksheet Section and/or a QA Assessment Worksheet) may comprise patient information (e.g., comprising patient name, age, gender, date of birth, accession number), a control (e.g., a slider control as shown in FIG. 11) for marking the exam object as "clinical" or "educational"), a tool for selecting an exam type to be associated with the exam object, a search or selection tool for adding, removing, or updating one or more tags (e.g., which may comprise an Exam State or other tag described herein) for the exam object, and/or a tool to identify a user (e.g., based on user role) to be assigned or associated with the exam object, which may affect the contextual processes or method steps employed by the platform, system, or method (e.g., as described herein).

Figure 12:
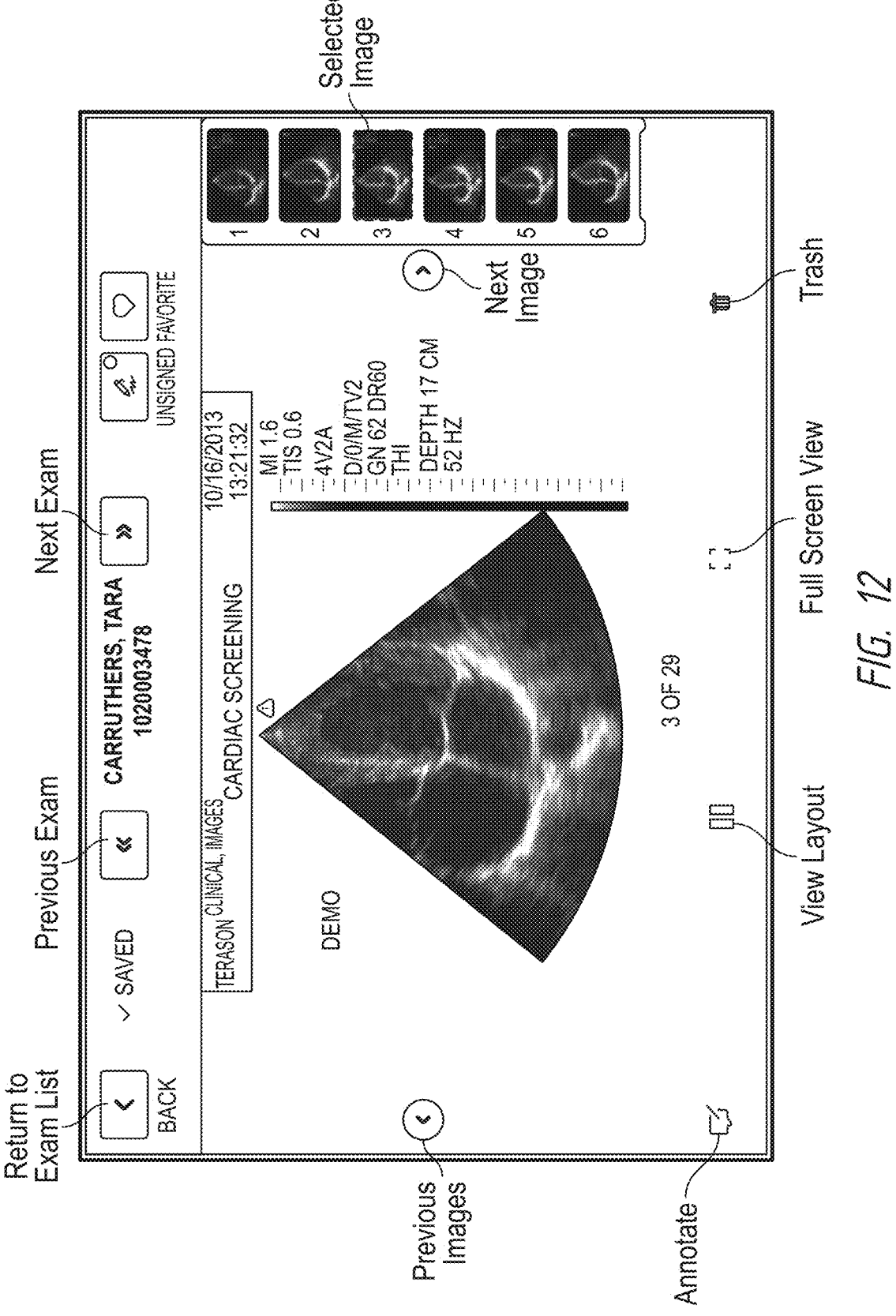
FIG. 12 shows a non-limiting example of an Image Review Screen of an Exam Review Screen, in accordance with some embodiments.
Figure 13:
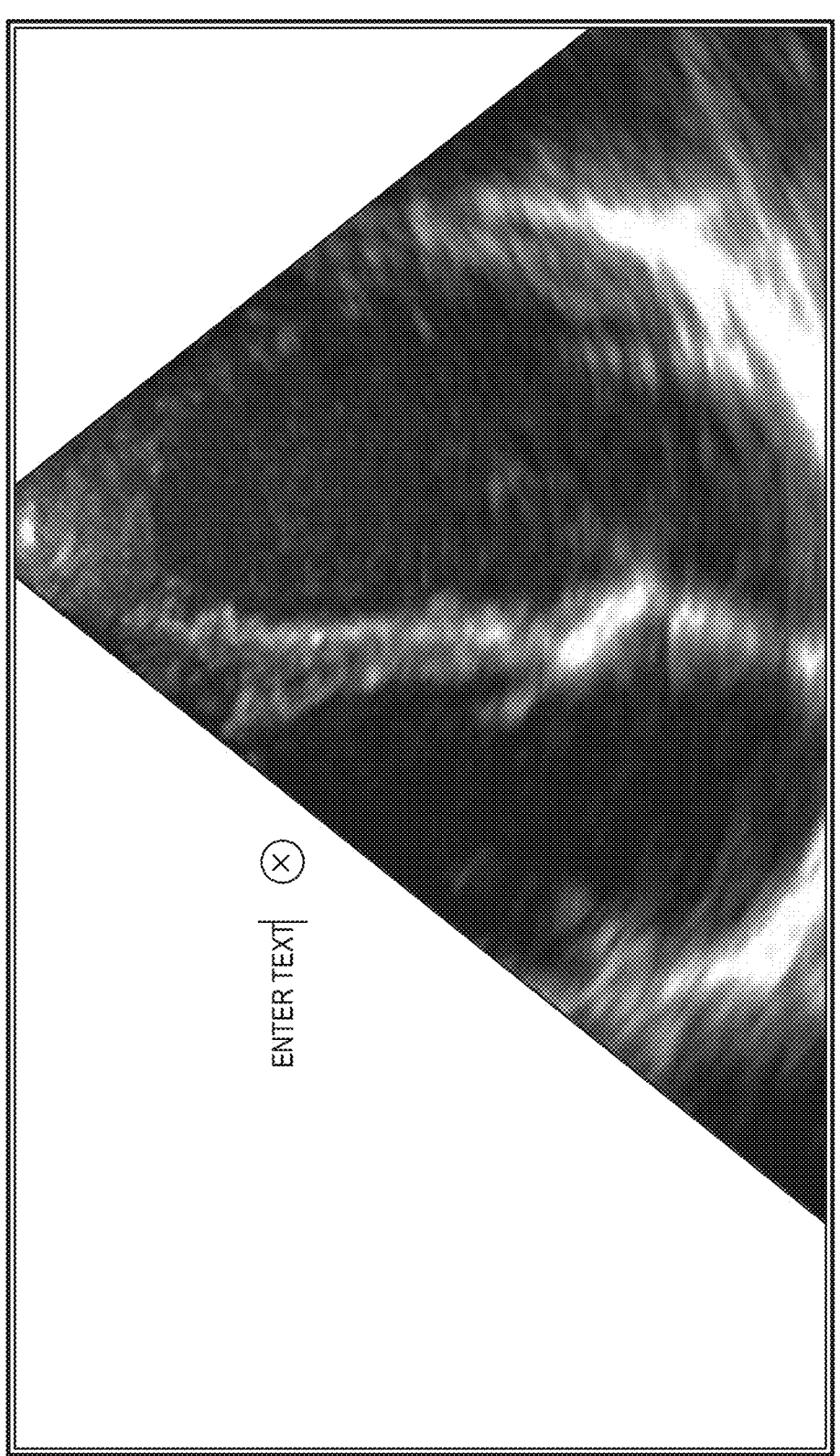
FIG. 13 shows a non-limiting example of an examination object annotation tool, in accordance with some embodiments.

As shown in FIG. 12, an Image Review Screen of an Exam Review Screen can display one or more images and/or video clips of an exam object. In some cases, an Image Review Screen can comprise one or more of a button for returning to an exam card or exam list selection screen (e.g., of an Exam Folder Menu), one or more buttons for cycling to the next or to the previous exam object in a list of exam objects (e.g., as determined by one or more search terms input by a user in a search field or tag field of the Exam Folder Menu), one or more buttons for cycling to the next or to the previous image (e.g., static image) or image clip (e.g., video image) of the selected exam object, one or more preview thumbnails of one or more next or previous images or image clips of the selected exam objects (e.g., wherein one of the plurality of preview thumbnails may be highlighted to indicate which image or image clip is currently selected, for example, as shown in FIG. 12), a button to access menu for annotating the selected image or image video clip (e.g., to add text to the image or image video clip, for example, as shown in FIG. 13), a button to access available layout view options (e.g., for viewing one or more images or image clips of the exam object one at a time or in a tiled view), controls for playing, pausing, skipping, and/or scanning through a selected image video clip, a button to access full-screen view of the selected image or image clip, and/or a button for deleting one or more images or image clips of the exam object, e.g., as shown in FIG. 12.

Figures 14A, 14B:
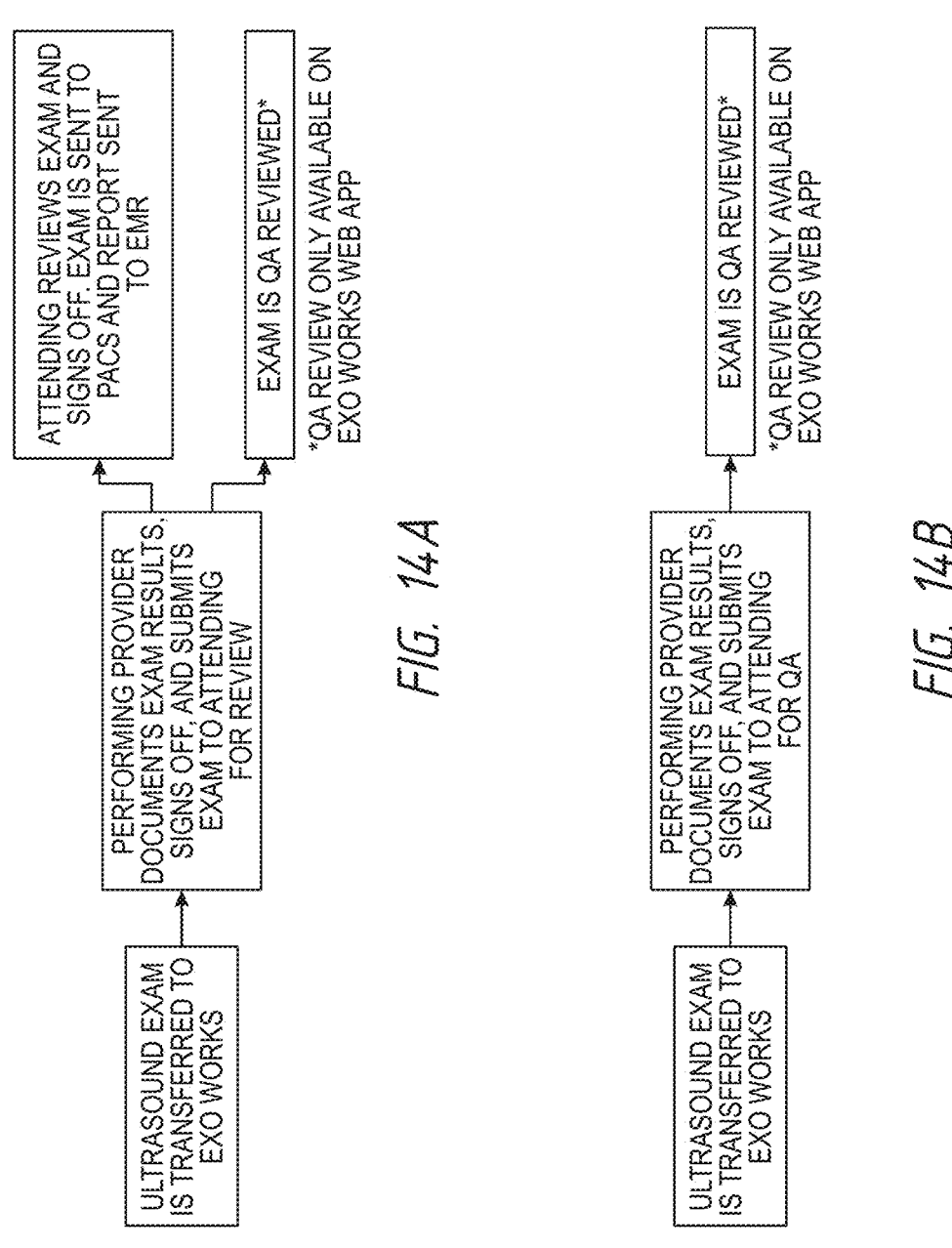
FIG. 14A shows a non-limiting example of a process comprising review and analysis of a clinical examination object, in accordance with some embodiments.
FIG. 14B shows a non-limiting example of a process comprising review and analysis of an educational examination object, in accordance with some embodiments.

As described herein, an exam object can be marked as "clinical" or "educational". In some cases, marking an exam object as "clinical" or as "educational" can change one or more steps, functionalities, or other aspects of the platform, system, or method (e.g., as described above and in FIG. 1A, FIG. 1B, FIG. 1C, and FIG. 1D). FIG. 14A shows an example of method steps that can be involved in the practice of a system, platform, or method described herein, e.g., wherein an exam object is marked as "clinical."

For example, an ultrasound exam object can be transferred to the client application of a platform, system, or method described herein, a performing user (e.g., a "performing provider") can review the exam object, analyzed the exam object, edit the exam object, provide an authorized signature for the exam object, and/or submit the exam object for review (e.g., by an attending user). In some cases, an exam object can be reviewed and, optionally interpreted and or edited, by an attending user.

In some cases, the attending user can provide an authorized signature and submit the exam object for archiving (e.g., at a PACS data store), for example, via an interpretation module of a server application. In some cases, a report updating an EMR database with respect to the analysis, interpretation, or contents of the exam object can be sent to the EMR database.

In some cases, the exam object can be marked as "clinical" upon receipt by the client application or a server application in communication with the client application and during the performing user review or the attending user review. In some cases, an exam object marked as "clinical" can undergo a QA review process (e.g., when the client application is a web application).

In some cases, a QA review process can be implemented (e.g., by a QA routing module) in parallel with an interpretation routing module of the server application. FIG. 14B shows an example of method steps that can be involved in the practice of a system, platform, or method described herein, e.g., wherein an exam object is marked as "educational."

In accordance with some embodiments, an ultrasound exam object can be transferred to the client application of a platform, system, or method described herein, a performing user (e.g., a "performing provider") can review the exam object, analyze the exam object, edit the exam object, provide an authorized signature for the exam object, and/or submit the exam object for review (e.g., by a QA Reviewer user). In some cases, the exam object marked as "educational" can under a QA review process (e.g., when the client application is a web application), for instance, after the performing user has completed one or more tasks with respect to the exam object (e.g., including providing an authorized signature).

Figure 15A:
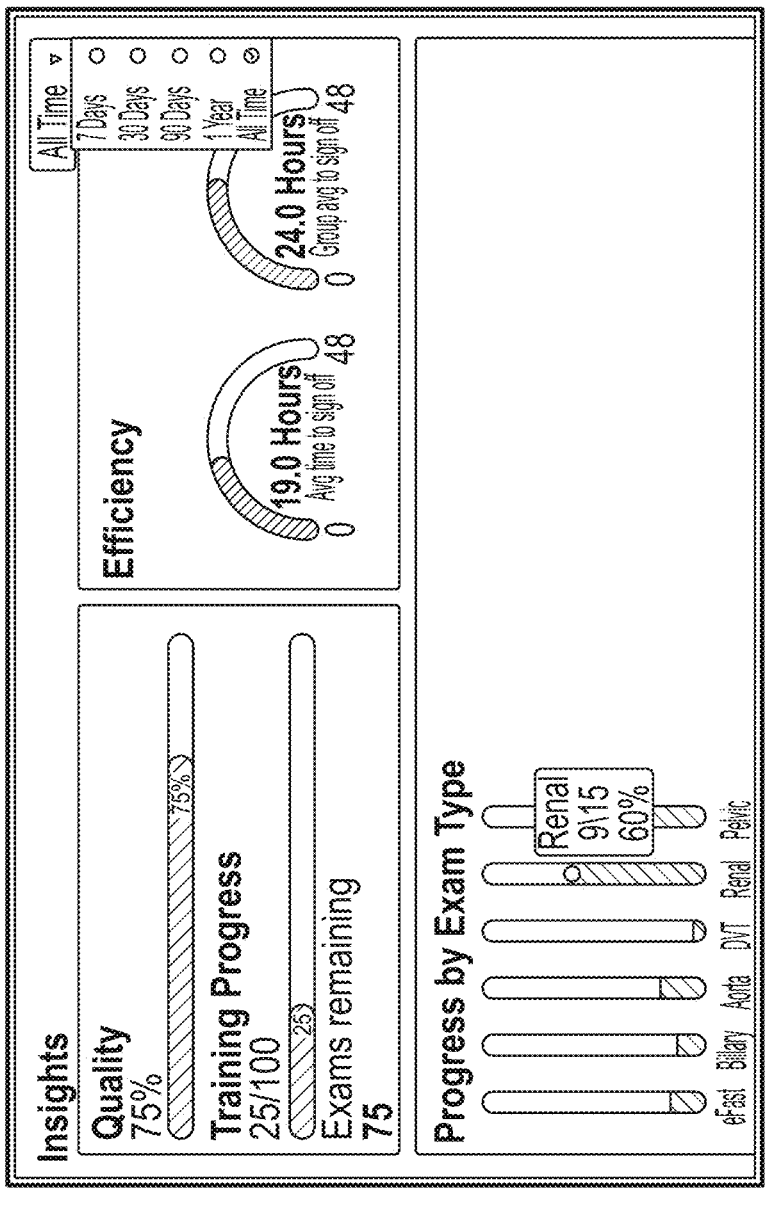
FIG. 15A shows a non-limiting example of an Insights analysis tool screen, in accordance with some embodiments.
Figure 15B:
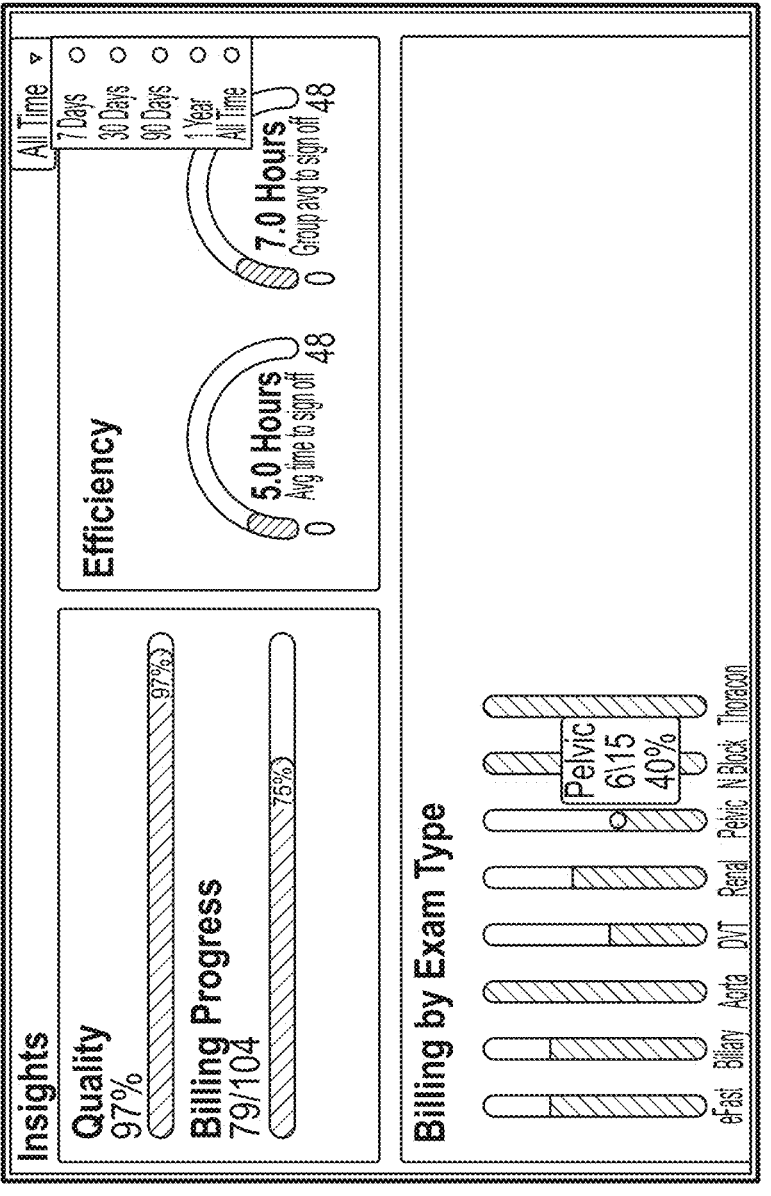
FIG. 15B shows a non-limiting example of an Insights analysis tool screen, in accordance with some embodiments.
Figure 15C:
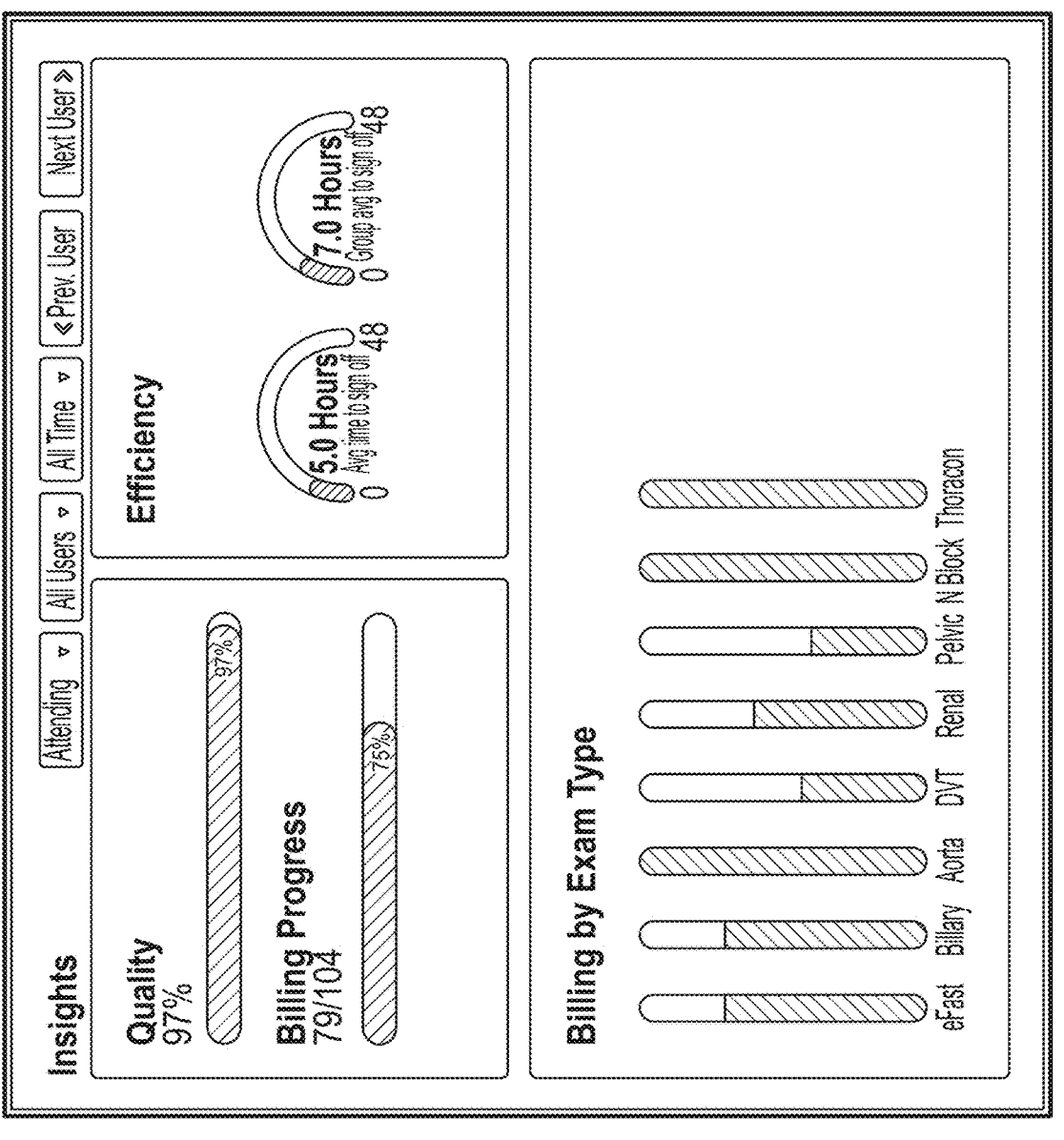
FIG. 15C shows a non-limiting example of an Insights analysis tool screen, in accordance with some embodiments.

Turning to FIG. 15A, FIG. 15B, and FIG. 15C, a platform, system, or method described herein can provide Insights analysis tools (e.g., of an Insights analysis suite) to a user (e.g., via a client application). In some cases, Insights analysis tools or a subset thereof can be made available (e.g., via a client application) to one or more non-credentialed users (e.g., as shown in FIG. 15A), one or more credentialed users (e.g., as shown in FIG. 15B), and/or one or more Clinical Admin users (e.g., as shown in FIG. 15C).

For example, it may be advantageous for non-credentialed users, who may not have authorization to analyze, interpret, and/or review an exam object, to have the ability to review or analyze metrics regarding system efficiency or quality or metrics regarding overall throughput (e.g., by type) using the system.

In some cases, a QA Reviewer user or Admin user may be a non-credentialed user. In some cases, Insights analysis tools (e.g., Insights analysis tools for non-credentialed users) can be used as part of a QA review process. As shown in FIG. 15A, FIG. 15B, and FIG. 15C, a quality score can be presented by the client application, for instance wherein the quality score presents a number of exam objects analyzed, completed, and/or reviewed over a specified date range meeting a quality standard (e.g., wherein the QA Reviewer user tasked with a QA process for the exam object in question has marked the exam object as meeting quality standards).

In some cases, a training progress score can be presented, for example, wherein the training progress score indicates a number of exam object analyses completed by a performing user as a fraction of a total number of exam object analysis required for the performing user's training to be complete.

In some cases, a progress score can be displayed, for example, wherein one or more progress indicators showing a number of exam object analyses completed by a performing user as fraction of one or more exam types required for a training or QA review of the performing user are presented (e.g., as shown in FIG. 15A).

In some cases, a billing score can be displayed, for example, wherein one or more progress indicators showing a number of exam object analyses have been billed as a fraction of an expected number of billed analyses per exam type are presented (e.g., as shown in FIG. 15B and FIG. 15C).

In some cases, an efficiency score can be presented, for example, wherein the efficiency score represents an average or median amount of time that a performing user spent to complete one exam object analysis (e.g., as evaluated over a specified period of time), for example as shown in FIG. 15A, FIG. 15B, and FIG. 15C.

In some cases, a text entry tool or date range selection tool can be provided to specify a period of time over which one or more analyses in the Insights screen is evaluated.

Figure 16:
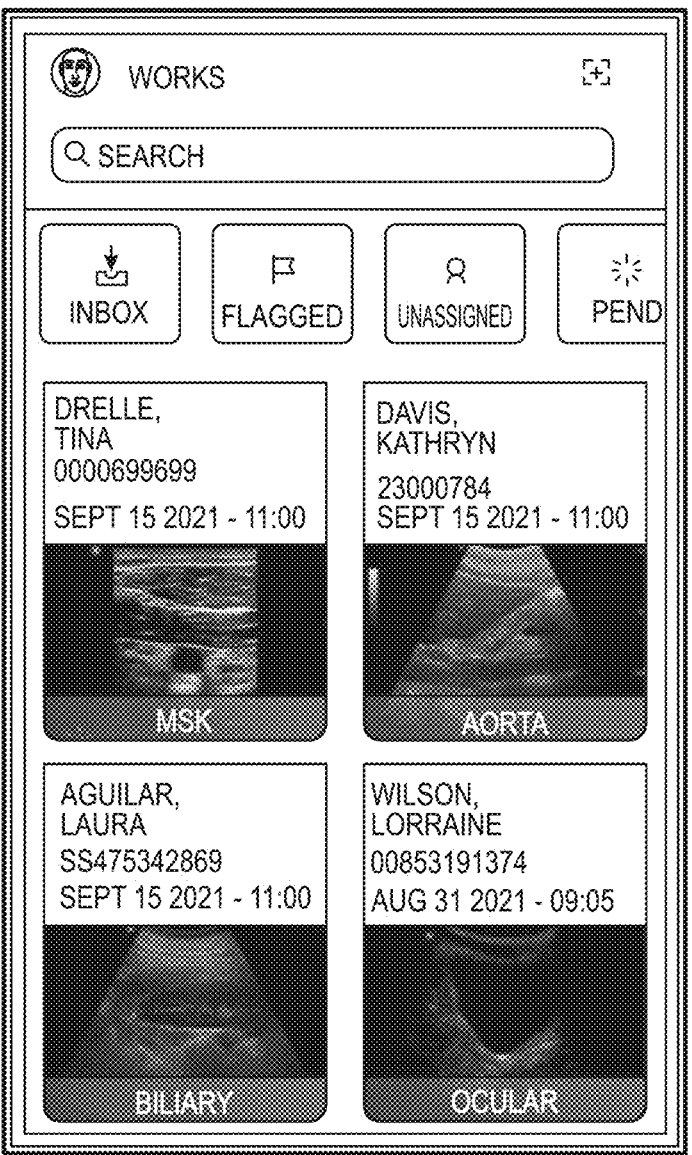
FIG. 16 shows a non-limiting example of a Folders Menu of a client application, in accordance with some embodiments.

Turning to FIG. 16, a Folders Menu of a client application, which can comprise one or more tabs that can be used to access exam object(s) marked according to the tabs' titles. In some cases, a Folders Menu can comprise one or more of an Inbox tab (e.g., for accessing exam objects requiring an action such as review, analysis, signature, or approval, by the logged-in user, who may be, e.g., a performing user or an attending user), a Flagged tab (e.g., for accessing exam objects requiring review of QA feedback), an Unassigned tab (e.g., for accessing exam objects that have not been assigned to a performing user), a Pending tab (e.g., for accessing exam objects that have been completed by the logged-in user and which may require a task to be completed by another user), a Favorites tab (e.g., for accessing exam objects marked by the logged-in user as a Favorite), an Archived tab (e.g., for accessing exam objects that have been completed and archived), and a Billed tab (e.g., for accessing exam objects that have been completed and for which CPT codes have been sent to an EMR for billing).

Figure 17:
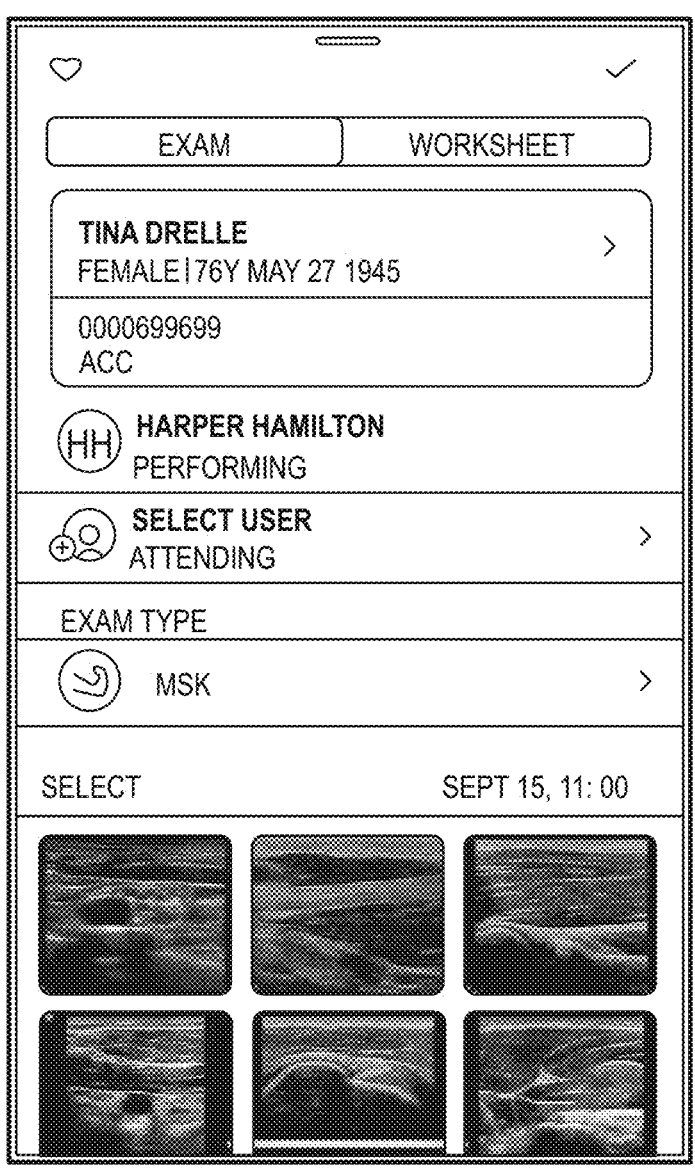
FIG. 17 shows a non-limiting example of an Exam Tab of a client application, in accordance with some embodiments.

FIG. 17 shows an example of an Exam Tab of a client application, in accordance with some embodiments. In some cases, an Exam Tab can be used to display patient information (e.g., comprising one or more of a patient's name, gender, date of birth, MRN number, and/or accession number).

In some cases, an individual can be assigned for one or more user roles associated with the exam object (e.g., performing user and/or attending user) via the Exam Tab. In some cases, an exam type can be defined for the exam object via the Exam Tab. In some cases, one or more images (e.g., static images) or image clips (e.g., video images) of the exam object can be selected and/or reviewed or analyzed using the Exam Tab.

Figure 18:
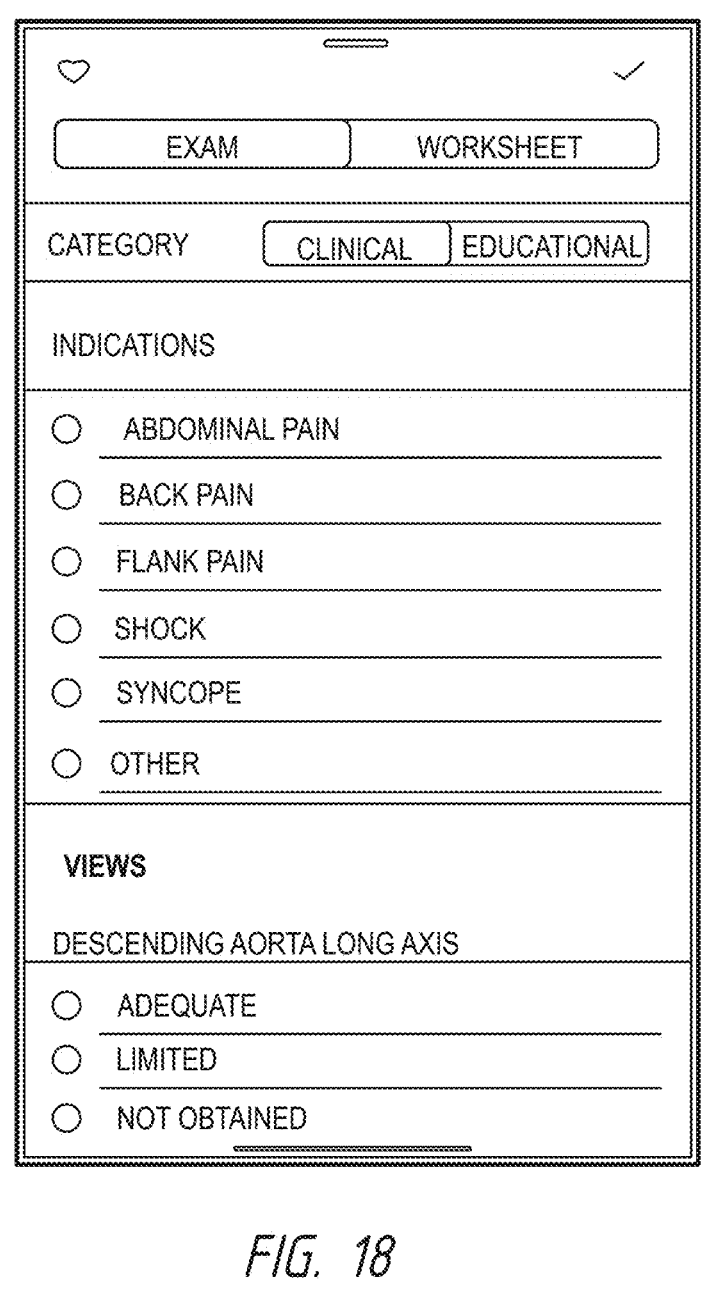

FIG. 18 shows an example of a Worksheet Tab of a client application, in accordance with some embodiments. In some cases, a Worksheet Tab can be used to add or modify analyses and/or markings (e.g., tags) associated with the exam object. For example, a Worksheet Tab can comprise selectors or text entry fields for marking an exam object as clinical or educational, for marking the exam object with one or more clinical indications, and for marking the exam object with one or more descriptive tags (e.g., image or image clip viewpoint perspective).

Ultrasound Exam Objects

The platforms, systems, and methods described herein can, in some embodiments, comprise one or more exam objects (e.g., examination objects). In some cases, an exam object can comprise medical data, metadata associated with medical data, and/or user-generated data pertaining to medical data. In some cases, an exam object can be an ultrasound exam object (e.g., an exam object defined by or related to ultrasound imaging data). In some cases, an exam object (e.g., an ultrasound exam object) can be generated and/or modified during a clinical evaluation of a patient, for example, during an ultrasound imaging examination of a patient. In some cases, an exam object can comprise a worksheet and/or one or more images (e.g., one or more ultrasound images).

In some cases, an image of an exam object can be generated by a medical imaging device, such as an ultrasound imaging device. In some cases, an exam object (e.g., an ultrasound exam object). In some cases, one or more images of an exam object can comprise (i) at least one static image, (ii) at least one video image, or (iii) both at least one static image and at least one video image.

In some cases, a worksheet of an exam object can comprise patient data, such as biographical data of the patient and/or medical history data of the patient. In some cases, a worksheet of an exam object can comprise exam data. In some cases, exam data can comprise metadata (e.g., comprising parameters or settings of a medical imaging device used to generate the exam object or a portion thereof), data generated and/or modified by one or more users (e.g., comprising data analysis), and/or data generated, maintained, and/or modified as a result of an action or lack thereof by an individual of a particular user role (e.g., exam object status).

User Roles

The platforms, systems, and methods described herein can, in some embodiments, comprise one or more user roles. In some cases, a user role can be (e.g., permanently or temporarily) assigned to one or more individuals, such as a clinical professional (e.g., a doctor or medical technician) or administrator. In some cases, a platform, system, or method described herein can comprise one or more user roles selected from: an administrator user, a performing user, an attending user, and/or a quality assurance (QA) reviewer user.

In some cases, an administrator user role can be a user role associated with administrative actions, such as assigning user role to one or more other individuals. In some cases, an administrator user role can be a Clinical Administrator User role (e.g., a Clinical Admin user). In some cases, an administrator user role can be an Information Technology Administrator User role (e.g., an IT Admin user).

In some cases, a performing user role can be assigned to an individual (e.g., a medical professional, such as a medical technician, a medical student, a nurse, a clinical intern, a clinical fellow, or medical resident) tasked with analyzing an exam object.

In some cases, an attending user role can be a user role assigned to an individual (e.g., an attending physician) tasked with interpretation of a work product of a performing user (e.g., interpretation of an analysis of an exam object).

In some cases, a plurality of user roles can be assigned to one individual (e.g., an administrator user and an attending user).

In some cases, a set of computer-implemented modules, functions, and/or privileges can be associated with (e.g., granted to) an individual user. For instance, a user role can allow access to and/or authority to modify a set of data (e.g., comprising one or more exam objects) and/or the ability to affect the status and/or transmission (e.g., routing) of the set of data. In some cases, a user role can restrict access to and/or authority to modify a set of data (e.g., comprising one or more exam objections) and/or the ability to affect the status and/or transmission (e.g., routing) of the set of data. For instance, a user role (e.g., a performing user) may be restricted from performing one or more actions with respect to the set of data (e.g., wherein a performing user is restricted from removing an exam object from a "Flagged" folder of a system or method without opening the exam object).

In some cases, one or more user roles of a system, platform, or method described herein can be stored on a data store of the system, platform, or method. For instance, a server application can comprise and/or access a data store comprising one or more user roles described herein.

In some cases, a server application can route (e.g., transmit or pass) one or more user roles to a client application (e.g., a user role module of a client application described herein), for instance from a data store (e.g., wherein the data store is part of or accessed by the server application). In some cases, a server application can route (e.g., transmit or pass) one or more user roles from a client application (e.g., a user role module of a client application) to a data store (e.g., of a server application). In some cases, a user role module of a client application can be used (e.g., by an authorized user, which can be an administrator user or an attending user) to assign one or more roles to one or more individuals (e.g., users).

Folders

The platforms, systems, and methods described herein can, in some embodiments, comprise one or more folder. For example, information, which may comprise all or a portion of an exam object can be stored permanently or temporarily in a folder. In some cases, a folder can be located in an ultrasound management module (e.g., of a client application of a platform or system described herein).

In some cases, a folder can be located in a data store (e.g., of a server application) of a platform or system described herein. In some cases, a platform, system, or method described herein can comprise a "Favorites" folder (e.g., a "Performing Favorites" folder), an "All Exams" folder, a "Tags" folder, an "Unassigned" folder, a "Performing Inbox" folder (e.g., a performing user's inbox folder), a "Performing Pending" folder (e.g., a performing user's pending folder), a "QA Pending" folder, a "QA Reviewer Inbox" folder (e.g., an inbox folder assigned to a QA Reviewer user), an "Attending Inbox" folder (e.g., an inbox folder assigned to an attending user), an "Attending Pending" folder (e.g., an attending user's pending folder), an "Archived" folder (e.g., a "Performing Archived" folder, which may be an archive folder assigned to a performing user), a "Flagged" folder (e.g., a "Performing Flagged" folder, which may be a flagged folder assigned to a performing user, an "Attending Flagged" folder, which may be a flagged folder assigned to an attending user, a "Clinical Admin Flagged" folder, which may be a flagged folder assigned to a Clinical Admin user), or a "Tags" folder, e.g., as shown in FIG. 3.

In some cases, a server application can route an exam object in a "Performing Favorites" folder, e.g., when a performing user toggles or selects a "favorites" control to an "on" value for the exam object. In some cases, a server application can remove an exam object from the "Performing Favorites" folder when a "favorites control is toggles or selected to an "off" value (e.g., by the performing user), for instance, as shown in FIG. 3.

In some cases, a provider (e.g., a performing user or an attending user) may be granted access to an "All Exams" folder, which can comprise one or more exam objects. In some cases, some or all exam objects can be added to the "All Exams" folder upon being received by a server application or a client application.

In some cases, a client application or a server application can allow a provider (e.g., a performing user or an attending user) to "tag" (e.g., mark or label) one or more exam objects with one or more "tag names" (e.g., Exam State values, facility locations, provider specialties, and/or other search terms). For instance, a provider can select a "Tags" folder to select one or more tags from a "drawer" of possible exam object "tags" (e.g., Exam States values, facility locations, provider specialties, and/or other search terms). In some cases, selecting one or more "tags" can cause a client application or server application to display or access all or a portion of the exam reports comprising the one or more "tags." In some cases, one or more "tags" of a "Tags" folder can be search terms, which can be selected by a user (e.g., via a client application) to locate or select an exam object or to narrow a search for one or more exam objects in a data store.

In some cases, a platform, system, or method can comprise an "Unassigned" folder, which can comprise exam objects for which a performing user has not been assigned or for which a performing user assigned to the exam object does not match performing user list of a database. In some cases, an "Unassigned" folder can be located in "Explorer" sections folder(s).

In some cases, an exam object can be routed to and/or from a folder by an assignment routing module (e.g., of a server application of a system, platform, or method described herein), by an interpretation routing module (e.g., of a server application of a system, platform, or method described herein), and/or by a Quality Assurance (QA) routing module (e.g., of server application of a system, platform, or method described herein).

Computing System

Figure 19:
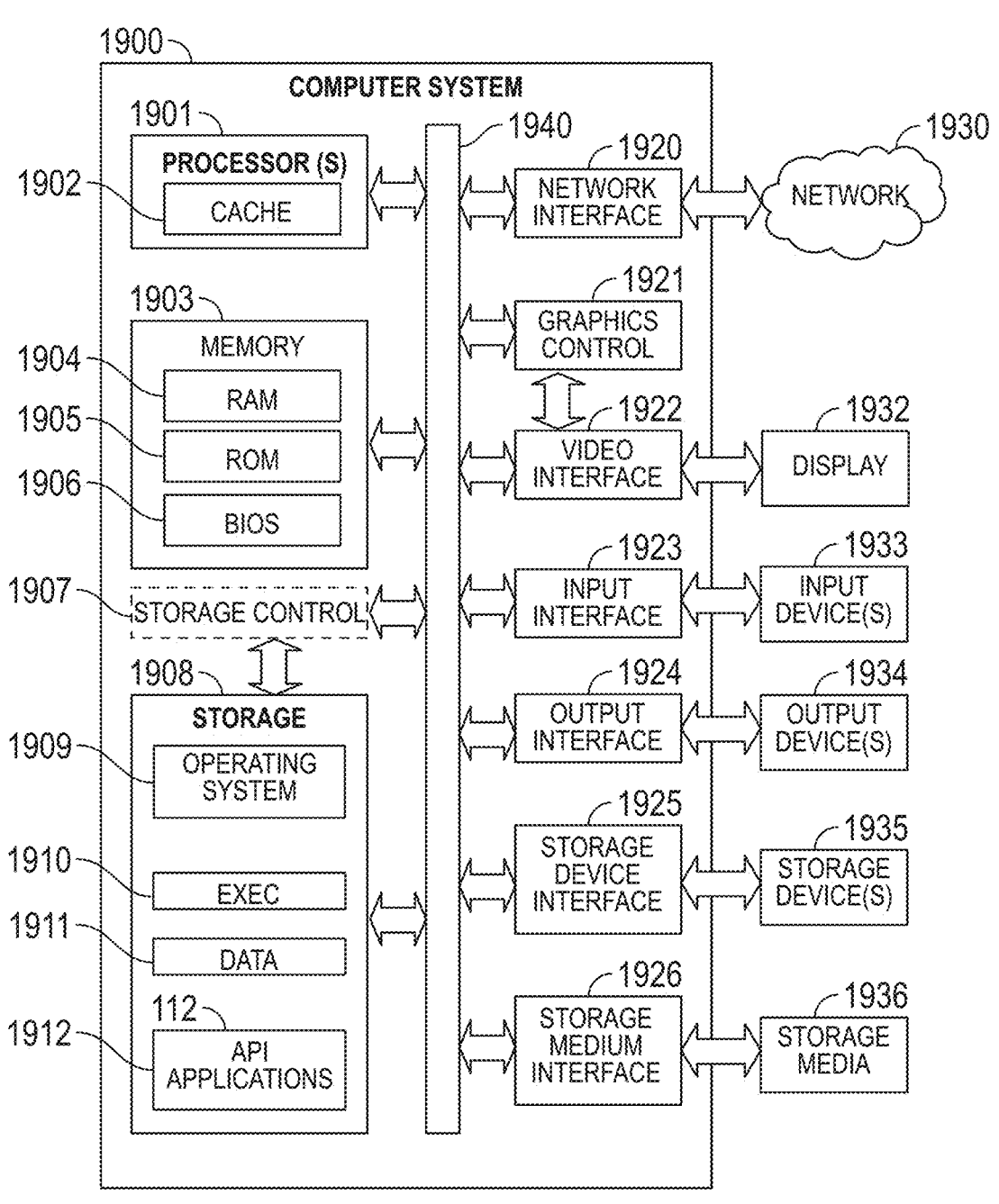
FIG. 19 shows a non-limiting example of a computing device, in accordance with some embodiments. In this figure, a device with one or more processors, memory, storage, and a network interface, in accordance with some embodiments.

Referring to FIG. 19, a block diagram is shown depicting an exemplary machine that includes a computer system 1900 (e.g., a processing or computing system) within which a set of instructions can execute for causing a device to perform or execute any one or more of the aspects and/or methodologies for static code scheduling of the present disclosure. The components in FIG. 19 are examples only and do not limit the scope of use or functionality of any hardware, software, embedded logic component, or a combination of two or more such components implementing particular embodiments.

Computer system 1900 may include one or more processors 1901, a memory 1903, and a storage 1908 that communicate with each other, and with other components, via a bus 1940. The bus 1940 may also link a display 1932, one or more input devices 1933 (which may, for example, include a keypad, a keyboard, a mouse, a stylus, etc.), one or more output devices 1934 (e.g., peripheral devices), one or more storage devices 1935, and various tangible storage media 1936. All of these elements may interface directly or via one or more interfaces or adaptors to the bus 1940. For instance, the various tangible storage media 1936 can interface with the bus 1940 via storage medium interface 1926. Computer system 1900 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 1900 includes one or more processor(s) 1901 (e.g., central processing units (CPUs), general purpose graphics processing units (GPGPUs), or quantum processing units (QPUs)) that carry out functions. Processor(s) 1901 optionally contains a cache memory unit 1902 for temporary local storage of instructions, data, or computer addresses. Processor(s) 1901 are configured to assist in execution of computer readable instructions. Computer system 1900 may provide functionality for the components depicted in FIG. 19 as a result of the processor(s) 1901 executing non-transitory, processor-executable instructions embodied in one or more tangible computer-readable storage media, such as memory 1903, storage 1908, storage devices 1935, and/or storage media 1936. The computer-readable media may store software that implements particular embodiments, and processor(s) 1901 may execute the software. Memory 1903 may read the software from one or more other computer-readable media (such as the storage device(s) 1935, 1936) or from one or more other sources through a suitable interface, such as network interface 1920. The software may cause processor(s) 1901 to carry out one or more processes or one or more steps of one or more processes described or illustrated herein. Carrying out such processes or steps may include defining data structures stored in memory 1903 and modifying the data structures as directed by the software.

The memory 1903 may include various components (e.g., machine readable media) including, but not limited to, a random access memory component (e.g., RAM 1904) (e.g., static RAM (SRAM), dynamic RAM (DRAM), ferroelectric random access memory (FRAM), phase-change random access memory (PRAM), etc.), a read-only memory component (e.g., ROM 1905), and any combinations thereof. ROM 1905 may act to communicate data and instructions unidirectionally to processor(s) 1901, and RAM 1904 may act to communicate data and instructions bidirectionally with processor(s) 1901. ROM 1905 and RAM 1904 may include any suitable tangible computer-readable media described below. In one example, a basic input/output system 1906 (BIOS), including basic routines that help to transfer information between elements within computer system 1900, such as during start-up, may be stored in the memory 1903.

Fixed storage 1908 is connected bidirectionally to processor(s) 1901, optionally through storage control unit 1907. Fixed storage 1908 provides additional data storage capacity and may also include any suitable tangible computer-readable media described herein. Storage 1908 may be used to store operating system 1909, executable(s) 1910, data 1911, applications 1912 (application programs), and the like. Storage 1908 can also include an optical disk drive, a solid-state memory device (e.g., flash-based systems), or a combination of any of the above. Information in storage 1908 may, in appropriate cases, be incorporated as virtual memory in memory 1903.

In one example, storage device(s) 1935 may be removably interfaced with computer system 100 (e.g., via an external port connector (not shown)) via a storage device interface 1925. Particularly, storage device(s) 1935 and an associated machine-readable medium may provide non-volatile and/or volatile storage of machine-readable instructions, data structures, program modules, and/or other data for the computer system 1900. In one example, software may reside, completely or partially, within a machine-readable medium on storage device(s) 1935. In another example, software may reside, completely or partially, within processor(s) 1901.

Bus 1940 connects a wide variety of subsystems. Herein, reference to a bus may encompass one or more digital signal lines serving a common function, where appropriate. Bus 1940 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 1900 may also include an input device 1933. In one example, a user of computer system 1900 may enter commands and/or other information into computer system 1900 via input device(s) 1933. Examples of an input device(s) 1933 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 1933 may be interfaced to bus 1940 via any of a variety of input interfaces 1923 (e.g., input interface 1923) including, but not limited to, serial, parallel, game port, USB, FIREWIRE, THUNDERBOLT, or any combination of the above.

In particular embodiments, when computer system 1900 is connected to network 1930, computer system 1900 may communicate with other devices, specifically mobile devices and enterprise systems, distributed computing systems, cloud storage systems, cloud computing systems, and the like, connected to network 1930. Communications to and from computer system 1900 may be sent through network interface 1920.

For example, network interface 1920 may receive incoming communications (such as requests or responses from other devices) in the form of one or more packets (such as Internet Protocol (IP) packets) from network 1930, and computer system 1900 may store the incoming communications in memory 1903 for processing. Computer system 1900 may similarly store outgoing communications (such as requests or responses to other devices) in the form of one or more packets in memory 1903 and communicated to network 1930 from network interface 1920. Processor(s) 1901 may access these communication packets stored in memory 1903 for processing.

Examples of the network interface 1920 include, but are not limited to, a network interface card, a modem, and any combination thereof. Examples of a network or network segment 1930 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 1930, may employ a wired and/or a wireless mode of communication. In general, any network topology may be used.

Information and data can be displayed through a display 1932. Examples of a display 1932 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 1932 can interface to the processor (s) 1901, memory 1903, and fixed storage 1908, as well as other devices, such as input device(s) 1933, via the bus 1940. The display 1932 is linked to the bus 1940 via a video interface 1922, and transport of data between the display 1932 and the bus 1940 can be controlled via the graphics control 1921. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 1932, computer system 1900 may include one or more other output devices 1934 (e.g., peripheral devices) including, but not limited to, an audio speaker, a printer, a storage device, and any combinations thereof. Such peripheral output devices may be connected to the bus 1940 via an output interface 1924. Examples of an output interface 1924 include, but are not limited to, a serial port, a parallel connection, a USB port, a FIREWIRE port, a THUNDERBOLT port, and any combinations thereof.

In addition or as an alternative, computer system 1900 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft®

Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® P54®, Microsoft® Xbox 360®, Microsoft Xbox One, Nintendo® Wii®, Nintendo® Wii U®, and Ouya®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In some cases, a computer program can comprise a client application and/or a server application described herein. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In some cases, a client application described herein can be a web application. In some cases, a web application (e.g., a client application) can interface with (e.g., communicate with) a server application described herein. In light of the disclosure provided herein, those of skill in the art will recognize that a web application, in various embodiments, utilizes one or more software frameworks and one or more database systems.

In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, XML, and document oriented database systems.

In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof.

In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash HTML 5, Apple® QuickTime®, Microsoft® Silverlight®, Java™, and Unity®.

Figure 20:
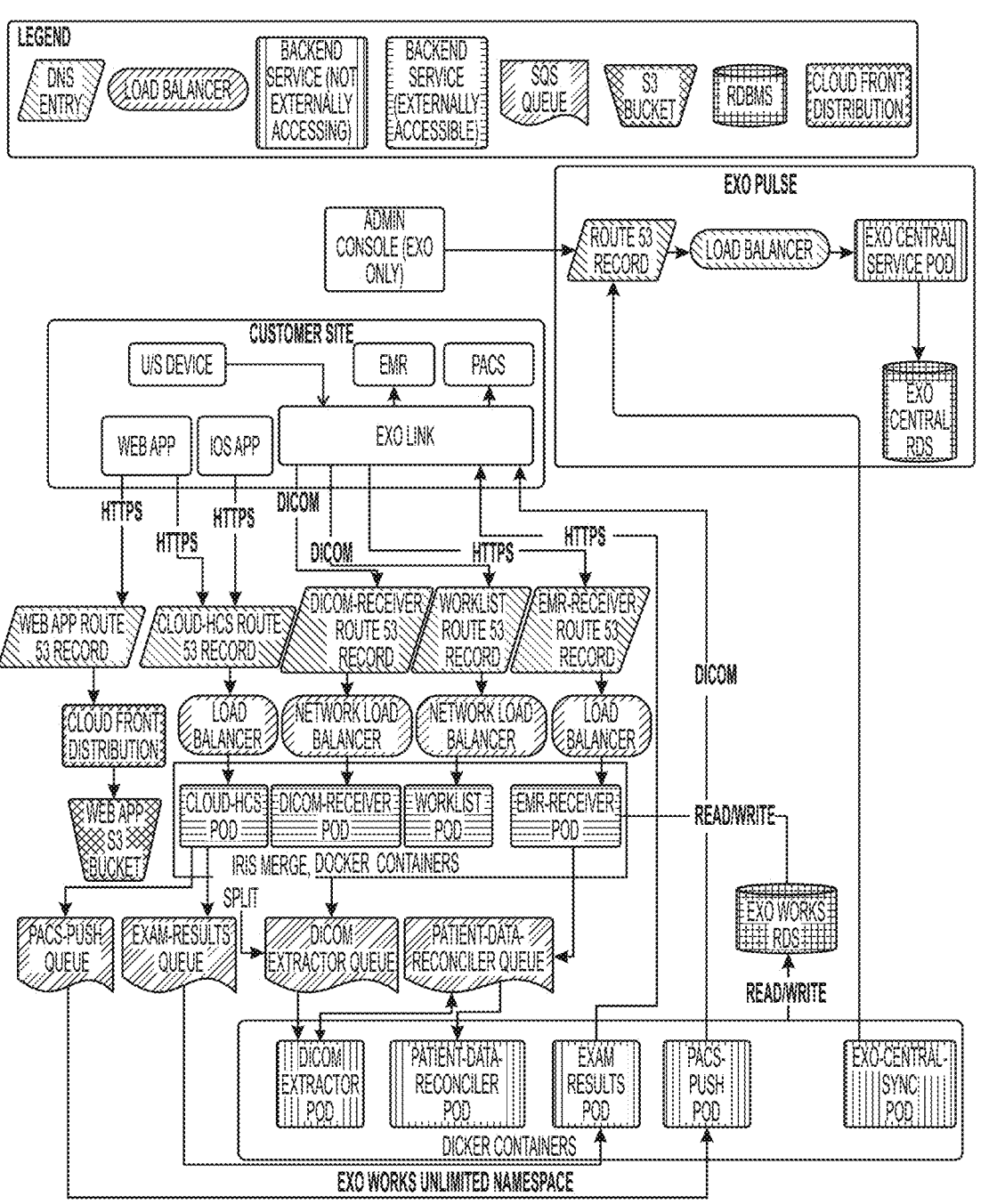
FIG. 20 shows a non-limiting example of a web/mobile application provision system, in accordance with some embodiments. In this figure, a system can include browser-based and/or native mobile user interfaces, in accordance with some embodiments.

FIG. 20 shows an example of a web or mobile application provision system of a platform, system, or method described herein. In some cases, a customer-facing portion ("Customer Site") of a web or mobile application provision system can comprise a native mobile device user interface (e.g., "iOS App") or a browser-based website (e.g., a "Web app"). In some cases, the Customer Site can comprise a server application (e.g., "Exo Link"). In some cases, the server application can receive data (e.g., comprising one or more images and one or more worksheets), for example from an ultrasound imaging device ("U/S Device"). In some cases, the server application can receive data from or transmit data to a database (e.g., an EMR database) and/or a data store (e.g., a PACS data store).

In some cases, a website application can transmit data to a web application DNS entry record module 2001 ("web app route 53 record"), for example, via a Hypertext Transfer Protocol Secure (HTTPS) formatted transmission. In some cases, the web application DNS entry record module can transmit the data to a content distribution module 2015 (e.g., a CloudFront distribution module).

In some cases, the content distribution module 2015 can transmit data to a data store (e.g., a cloud-based data store 2013, such as a web app Amazon S3 bucket). In some cases, the Web app (and/or an iOS App) can transmit data to a cloud-based DNS entry record module ("cloud-hcs route 53 record"). In some cases, the cloud-based DNS entry record module can pass the data to a load balancer 2008. In some cases, the load balancer 2008 can pass the data to a pod (e.g., a cloud-based hcs pod docket container).

In some cases, a pod (e.g., an externally accessible cloud-based pod docket container 2011) can pass data to a queue service module 2012 (e.g., a simple queue service (SQS), such as a "PACS-push queue"). In some cases, the queue service module can transmit data to a push notification pod (e.g., a data store push notification pod, "PACS-push pod", which may in some cases not be externally accessible) In some cases, the push notification pod can transmit data to the server application, which can, in some cases, transmit the data (e.g., comprising a push notification) to a PACS data store.

In some cases, the externally accessible cloud-based pod (e.g., "cloud-hcs pod") can transmit data (e.g., comprising an exam object or portion thereof) to a queue service module 2012 (e.g., "exam-results queue"), which may be different than the data store push queue. In some cases, the exam results queue can transmit data to a pod 2010 (e.g., an exam results pod, "exam-results pod", which may in some cases not be externally accessible). In some cases, the exam results pod can transmit data to the server application, which can, in some cases, transmit the data to a database. In some cases, the externally accessible cloud-based pod 2011 (e.g., "cloud-hcs pod") can transmit data to a DICOM extractor queue service module ("dicom extractor queue"). In some cases, the DICOM extractor queue service module can transmit data to a pod 2010 (e.g., a DICOM extractor pod, "dicom-extractor pod", which may in some cases not be externally accessible). In some cases, the DICOM extractor pod can transmit data to a patient data reconciler queue service module, which can, in some cases, transmit data to a patient data reconciler pod (e.g., which may in some cases not be externally accessible).

In some cases, a server application can transmit data to one or more of a DICOM-receiver DNS entry record module (e.g., via DICOM formatted transmission), a worklist DNS entry record module (e.g., via DICOM formatted transmission), and/or a database receiver DNS entry record module (e.g., via an HTTPS formatted transmission). In some cases, a DNS entry record module can be used to log an Internet Protocol (IP) address of a device transmitting data to the DNS entry record module. In some cases, a DNS entry record module 2001 (e.g., a DICOM receiver DNS entry record module, e.g., "dicom-receiver route 53 record", worklist DNS entry record module, e.g., "worklist route 53 record, and/or a database DNS entry record module, e.g., "emr-receiver route 53 record") can transmit data to the same or a different load balancer 2008 (e.g., a network load balancer), which can, in some cases, transmit data to a pod (e.g., an externally accessible pod 2011) of the platform, system, or method.

For example, a DICOM receiver DNS entry record module can transmit data to a DICOM receiver pod (e.g., "dicom-receiver pod") via a network load balancer. In some cases, a worklist DNS entry record module can transmit data to a worklist pod (e.g., "worklist pod") via a network load balancer. In some cases, a database DNS entry record module can transmit data to a database receiver pod (e.g., "emr-receiver pod") via a load balancer 2008. In some cases, a DICOM receiver pod can transmit data to a DICOM extractor queue service module. In some cases, a database receiver pod can transmit data to a patient data reconciler queue service module (e.g., "patient-data-reconciler queue"). In some cases, a patient data reconciler queue service module can transmit data to a patient data reconciler pod (e.g., which may in some cases not be externally accessible).

In some cases, a web or mobile application provision system can comprise a synchronization pod (e.g., "exo-central-sync pod"), which may in some cases not be externally accessible. In some cases, the synchronization pod can transmit data to a DNS entry record module 2001 (e.g., "Route 53 record") of a central module of the system. In some cases, an administrator can transmit data to the DNS entry record module of the central module of the system, for example, via a console ("Admin console"). In some cases, the DNS entry record module of the central module of the system can transmit data to a load balancer 2008, which can, in some cases, transmit data to a pod (e.g., "Exo Central Service pod"). In some cases, the pod can transmit data to a database management service (e.g., a relational database management service 2014 (RDBMS)) of the central module (e.g., "Exo Central RDS").

In some cases, one or more docket containers (e.g., one or more externally accessible pods and/or one or more pods that are not externally accessible) can transmit read/write data to a database management service (e.g., relational database management service 2014 "Exo Works RDS").

Figure 21:
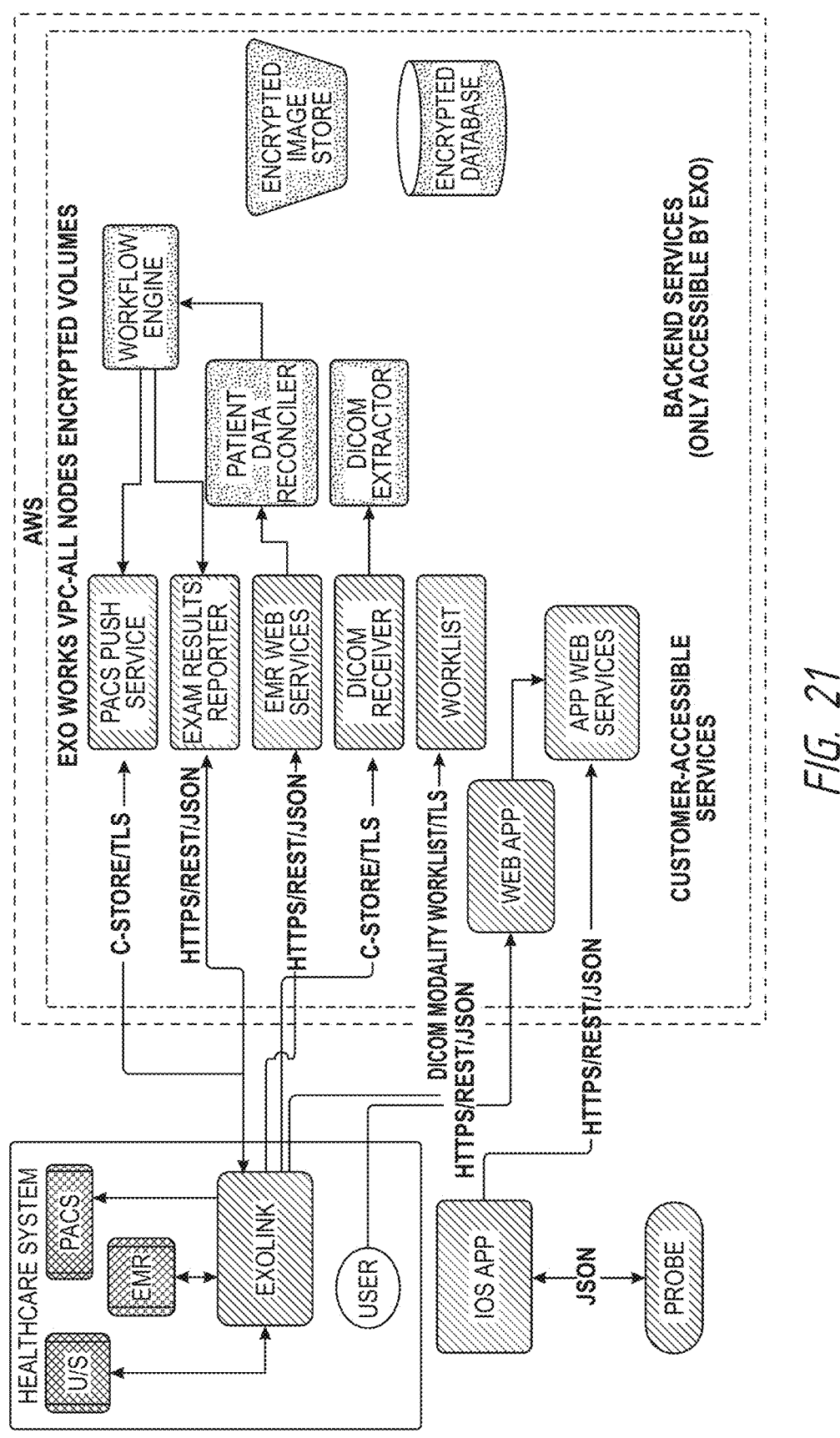
FIG. 21 shows a non-limiting example of a cloud-based web/mobile application provision system, in accordance with some embodiments. In this figure, a system can comprise an elastically load balanced, auto-scaling web server and application server resources as well synchronously replicated databases, in accordance with some embodiments.

FIG. 21 shows an example of a cloud-based web or mobile application provision system (e.g., "Exo Works VPC") of a platform, system, or method described herein. In some cases, ultrasound imaging data (e.g., comprising one or more static images and/or one or more video images) can be transmitted from an ultrasound device (e.g., a probe of an ultrasound device) to a mobile ultrasound data acquisition application (e.g., in JavaScript Object Notation (JSON) format).

In some cases, the mobile ultrasound data acquisition application can transmit the ultrasound imaging data to an application web service of a server application of a platform, system, or method described herein (e.g., in Hypertext Transfer Protocol (HTTP), Hypertext Transfer Protocol Secure (HTTPS), Representative State Transfer (REST), or JSON format). In some cases, the server application can be hosted on a cloud-based provision system (e.g., comprising cloud-hosted computing platforms and application programming interfaces (APIs)), such as Amazon Web Services (AWS). In some cases, a user, which may be part of a healthcare system (e.g., in a user role as a performing user, an attending user, and administrator user, or a QA reviewer user), can access the cloud-based web or mobile application via a web application or a mobile application (e.g., which may be hosted on the cloud-based provision system), for example using one or more input/output format selected from HTTPS, REST, or JSON.

In some cases, an ultrasound device ("U/S"), a data store (e.g., a PACS data store), and/or a database (e.g., an EMR database), which may be part of the healthcare system, can connect to the cloud-based web or mobile application via a server application (e.g., "Exo Link").

In some cases, data from the server application can route data to one or more modules of the cloud-hosted portion of the cloud-based web or mobile application (e.g., via HTTPS, REST, or JSON formatted transmissions). In some cases, the server application can (e.g., automatically) transmit data (e.g., data from a database, wherein the data may comprise patient data (e.g., comprising Protected Health Information (PHI)) to a modality worklist of the cloud-based web or mobile application (e.g., via a DICOM modality worklist (e.g., with a secure transport layer security (TLS) communication protocol)). In some cases, the server application can transmit data to a DICOM receiver of the cloud-based web or mobile application (e.g., via a DICOM push operation (e.g., C-STORE)). In some cases, the DICOM push operation can be passed from the DICOM receiver to a DICOM extractor (e.g., for extraction of some or all of the DICOM-encoded data, which may comprise one or more images) and, in some cases, on to a Patient Data Reconciler.

In some cases, the extracted data can be transmitted from the Patient Data Reconciler to a Workflow Engine of the cloud-based web or mobile application of the platform, system, or method. In some cases, the server application can transmit data to a database web services module of the cloud-based web or mobile application (e.g., an EMR Web Services module), for example, via an HTTPS, REST, or JSON formatted transmission. In some cases, the database web services module can pass data to the patient data reconciler. In some cases, the patient data reconciler can pass the data from the database web services module to the workflow engine.

In some cases, the workflow engine can transmit data to a database push service module (e.g., PACS Push Service module), which can transmit information (e.g., in the form of a TLS formatted C-STORE DICOM push operation) to the server application, in some embodiments. In some cases, the workflow engine can transmit data to an exam results reporter module, which can transmit information to the server application (e.g., in the form of an HTTPS, REST, or JSON formatted transmission).

In some embodiments, a cloud-hosted portion of the cloud-based web or mobile application can comprise a data store (e.g., an encrypted image store) and/or a database (e.g., an encrypted database), for example, to store one or more of patient data, ultrasound imaging data, and/or user-generated data, which can include analysis, tags, and/or feedback generated by one or more users.

In some cases, one or more backend services of the cloud-hosted portion of the cloud-based web or mobile application (e.g., including one or more of a DICOM extractor, a Patient Data Reconciler, a Workflow Engine, a data store, and/or a database) may be accessible by the application but not by a user. In some cases, one or more services or modules of a cloud-hosted portion of a cloud-based web or mobile application (e.g., including one or more of a web application, the application web services, a modality worklist, a DICOM receiver, the database web services, an exam results reporter, and/or a data push service module) can be accessible by the user.

Mobile Application

In some embodiments, a computer program includes a mobile application provided to a mobile computing device. In some cases, a client application described herein can be a mobile application. In some cases, a mobile application (e.g., a client application) can interface with (e.g., communicate with) a server application described herein. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. In some cases, a client application described herein can be a standalone application. In some cases, a standalone application (e.g., a client application) can interface with (e.g., communicate with) a server application described herein. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in (e.g., extension, etc.). In some cases, a client application described herein can be a web browser plug-in application. In some cases, a web browser plug-in application can interface with (e.g., communicate with) a server application described herein. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application.

For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected computing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile computing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, a distributed computing resource, a cloud computing resource, or combinations thereof. In further various embodiments, a software module comprises a plurality of files, a plurality of sections of code, a plurality of programming objects, a plurality of programming structures, a plurality of distributed computing resources, a plurality of cloud computing resources, or combinations thereof. In various embodiments, the one or more software modules comprise, by way of non-limiting examples, a web application, a mobile application, a standalone application, and a distributed or cloud computing application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of medical information, such as medical data, which can comprise medical images and/or medical records (e.g., comprising patient medical history information). In various embodiments, suitable databases include, by way of non-limiting examples, relational databases, non-relational databases, object-oriented databases, object databases, entity-relationship model databases, associative databases, XML databases, document-oriented databases, and graph databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing based. In a particular embodiment, a database is a distributed database. In other embodiments, a database is based on one or more local computer storage devices.

Certain Definitions

Unless otherwise defined, all technical terms used herein have the same meaning as commonly understood by one of ordinary skill in the art to which the present subject matter belongs.

As used in this specification and the appended claims, the singular forms "a," "an," and "the" include plural references unless the context clearly dictates otherwise. Any reference to "or" herein is intended to encompass "and/or" unless otherwise stated.

Reference throughout this specification to "some embodiments," "further embodiments," or "a particular embodiment," means that a particular feature, structure, or characteristic described in connection with the embodiment is included in at least one embodiment. Thus, the appearances of the phrase "in some embodiments," or "in further embodiments," or "in a particular embodiment" in various places throughout this specification are not necessarily all referring to the same embodiment. Furthermore, the particular features, structures, or characteristics may be combined in any suitable manner in one or more embodiments.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A platform for routing point of care ultrasound examinations in a computer network comprising: a plurality of computing devices, each computing device comprising at least one processor and instructions executable by the at least one processor to provide a client application comprising: a user role module configured to present a user interface allowing an administrator user to assign user roles to other users, the user roles comprising a performing user, an attending user, and a quality assurance (QA) reviewer user; an ultrasound management module configured to present an interface comprising folders for ultrasound exam objects, the folders comprising an inbox folder, a pending folder, and a flagged folder; and an ultrasound review module configured to present an interface comprising tools for reviewing ultrasound exam objects; and at least one server processor and instructions executable by the at least one server processor to provide a server application comprising: a data store comprising one or more assigned user roles; an interface module configured to communicate with at least one ultrasound imaging system and import an ultrasound exam object, the ultrasound exam object comprising a worksheet and one or more images; an assignment routing module configured to: assign the ultrasound exam object to a performing user, and route via the computer network the ultrasound exam object to a performing user's inbox folder to be completed; an interpretation routing module configured to: route via the computer network a completed ultrasound exam object to an attending user's inbox folder to be interpreted, and transfer the completed ultrasound exam object to a performing user's pending folder; and a QA routing module configured to: route via the computer network a completed ultrasound exam object to a QA reviewer's inbox folder to be reviewed, transfer the completed ultrasound exam object to the performing user's pending folder, and route via the computer network a reviewed ultrasound exam object to a performing user's flagged folder if the QA reviewer user requests feedback.

Clause 2. The platform of Clause 1, wherein the ultrasound exam object further comprises a type with a value of clinical or educational, wherein if the type has a value of educational the interpretation routing operation is suspended.

Clause 3. The platform of any of the preceding Clauses, wherein the one or more images comprise at least one static image, at least one video image, or both at least one static image and least one video image.

Clause 4. The platform of any of the preceding Clauses, wherein the worksheet comprises patient data and exam data.

Clause 5. The platform of Clause 4, wherein the tools for reviewing ultrasound exam objects allow a user to: view the one or more images, review the worksheet, edit the worksheet, view the patient data, edit the patient data, view the exam data, edit the exam data, and perform QA review.

Clause 6. The platform of any of the preceding Clauses, wherein one or more folders comprises a list view and a card view.

Clause 7. The platform of Clause 6, wherein each card in the card view comprises an exam status icon.

Clause 8. The platform of Clause 7, wherein the exam status icon indicates draft, pending, failed archive, educational, or archived status.

Clause 9. The platform of any of the preceding Clauses, wherein the interface comprising folders for ultrasound exam objects comprises a search element.

Clause 10. The platform of Clause 9, wherein the ultrasound exam object further comprises one or more tags.

Clause 11. The platform of Clause 10, wherein the search element allows a user to search by tag.

Clause 12. The platform of any of the preceding Clauses, wherein the interpretation routing module and the QA routing module operate in series, wherein the interpretation routing module operates before the QA routing module.

Clause 13. The platform of any of the preceding Clauses, wherein the interpretation routing module and the QA routing module operate in parallel.

Clause 14. The platform of any of the preceding Clauses, wherein the server application further comprises an interface module configured to communicate with at least one electronic medical record (EMR) system.

Clause 15. The platform of any of the preceding Clauses, wherein the server application further comprises an interface module configured to communicate with at least one electronic archive.

Clause 16. The platform of Clause 15, wherein the server application further comprises an archive routing module configured to route via the computer network the ultrasound exam object to the archive subsequent to completion, interpretation, and review.

Clause 17. The platform of Clause 15, wherein the interface comprising folders for ultrasound exam objects further comprises an archived folder.

Clause 18. The platform of Clause 15, wherein the archive comprises a picture archiving and communication system (PACS) or a vendor neutral archive (VNA).

Clause 19. The platform of any of the preceding Clauses, wherein the server application further comprises an insights module configured to calculate metrics over a plurality of ultrasound exam objects, the metrics comprising quality and efficiency.

Clause 20. The platform of Clause 19, wherein the client application further comprises an insights module configured to present a user interface allowing a user to view the metrics.

Clause 21. The platform of any of the preceding Clauses, wherein the user interface allowing an administrator user to assign user roles to other users further allows the administrator user to assign a point of care specialty and a facility to other users.

Clause 22. The platform of Clause 21, wherein the assignment routing module assigns the ultrasound exam object to a performing user at least in part based on point of care specialty and facility.

Clause 23. The platform of any of the preceding Clauses, wherein the interface comprising folders for ultrasound exam objects further comprises an unassigned folder.

Clause 24. The platform of any of the preceding Clauses, wherein the interface comprising folders for ultrasound exam objects further comprises a favorites folder, and wherein the interface comprising tools for reviewing ultrasound exam objects further comprises an element to mark an ultrasound exam object as a favorite.

Clause 25. The platform of any of the preceding Clauses, wherein the interface comprising folders for ultrasound exam objects further comprises a billed folder.

Clause 26. The platform of Clause 25, wherein the interpretation routing module is further configured to route via the computer network an interpreted and archived ultrasound exam object to an attending user's billed folder.

Clause 27. A computer-implemented system for routing point of care ultrasound examinations in a computer network comprising at least one processor and instructions executable by the at least one processor to provide an application comprising: a user role module configured to present a user interface allowing an administrator user to assign user roles to other users, the user roles comprising a performing user, an attending user, and a quality assurance (QA) reviewer user; a data store comprising one or more assigned user roles; an ultrasound management module configured to present an interface comprising folders for ultrasound exam objects, the folders comprising an inbox folder, a pending folder, and a flagged folder; an ultrasound review module configured to present an interface comprising tools for reviewing ultrasound exam objects; an interface module configured to communicate with at least one ultrasound imaging system and import an ultrasound exam object, the ultrasound exam object comprising a worksheet and one or more images; an assignment routing module configured to: assign the ultrasound exam object to a performing user, and route via the computer network the ultrasound exam object to a performing user's inbox folder to be completed; an interpretation routing module configured to: route via the computer network a completed ultrasound exam object to an attending user's inbox folder to be interpreted, and transfer the completed ultrasound exam object to a performing user's pending folder; and a QA routing module configured to: route via the computer network a completed ultrasound exam object to a QA reviewer's inbox folder to be reviewed, transfer the completed ultrasound exam object to the performing user's pending folder, and route via the computer network a reviewed ultrasound exam object to a performing user's flagged folder if the QA reviewer user requests feedback.

Clause 28. The system of Clause 27, wherein the ultrasound exam object further comprises a type with a value of clinical or educational, wherein if the type has a value of educational the interpretation routing operation is suspended.

Clause 29. The system of any of Clauses 27-28, wherein the one or more images comprise at least one static image, at least one video image, or both at least one static image and least one video image.

Clause 30. The system of any of Clauses 27-29, wherein the worksheet comprises patient data and exam data.

Clause 31. The system of Clause 30, wherein the tools for reviewing ultrasound exam objects allow a user to: view the one or more images, review the worksheet, edit the worksheet, view the patient data, edit the patient data, view the exam data, edit the exam data, and perform QA review.

Clause 32. The system of any of Clauses 27-31, wherein one or more folders comprises a list view and a card view.

Clause 33. The system of Clause 32, wherein each card in the card view comprises an exam status icon.

Clause 34. The system of Clause 33, wherein the exam status icon indicates draft, pending, failed archive, educational, or archived status.

Clause 35. The system of any of Clauses 27-34, wherein the interface comprising folders for ultrasound exam objects comprises a search element.

Clause 36. The system of Clause 35, wherein the ultrasound exam object further comprises one or more tags.

Clause 37. The system of Clause 36, wherein the search element allows a user to search by tag.

Clause 38. The system of any of Clauses 27-37, wherein the interpretation routing module and the QA routing module operate in series, wherein the interpretation routing module operates before the QA routing module.

Clause 39. The system of any of Clauses 27-38, wherein the interpretation routing module and the QA routing module operate in parallel.

Clause 40. The system of any of Clauses 27-39, wherein the application further comprises an interface module configured to communicate with at least one electronic medical record (EMR) system.

Clause 41. The system of any of Clauses 27-40, wherein the application further comprises an interface module configured to communicate with at least one electronic archive.

Clause 42. The system of Clause 41, wherein the application further comprises an archive routing module configured to route via the computer network the ultrasound exam object to the archive subsequent to completion, interpretation, and review.

Clause 43. The system of Clause 42, wherein the interface comprising folders for ultrasound exam objects further comprises an archived folder.

Clause 44. The system of Clause 42, wherein the archive comprises a picture archiving and communication system (PACS) or a vendor neutral archive (VNA).

Clause 45. The system of any of Clauses 27-44, wherein the application further comprises an insights module configured to calculate metrics over a plurality of ultrasound exam objects, the metrics comprising quality and efficiency.

Clause 46. The system of Clause 45, wherein the insights module is further configured to present a user interface allowing a user to view the metrics.

Clause 47. The system of any of Clauses 27-46, wherein the user interface allowing an administrator user to assign user roles to other users further allows the administrator user to assign a point of care specialty and a facility to other users.

Clause 48. The system of Clause 47, wherein the assignment routing module assigns the ultrasound exam object to a performing user at least in part based on point of care specialty and facility.

Clause 49. The system of any of Clauses 27-48, wherein the interface comprising folders for ultrasound exam objects further comprises an unassigned folder.

Clause 50. The system of any of Clauses 27-49, wherein the interface comprising folders for ultrasound exam objects further comprises a favorites folder, and wherein the interface comprising tools for reviewing ultrasound exam objects further comprises an element to mark an ultrasound exam object as a favorite.

Clause 51. The system of any of Clauses 27-50, wherein the interface comprising folders for ultrasound exam objects further comprises a billed folder.

Clause 52. The system of Clause 51, wherein the interpretation routing module is further configured to route via the computer network an interpreted and archived ultrasound exam object to an attending user's billed folder.

Clause 53. A computer-implemented method of routing point of care ultrasound examinations in a computer network comprising: providing a user interface allowing an administrator user to assign user roles to other users, the user roles comprising a performing user, an attending user, and a quality assurance (QA) reviewer user; maintaining a data store comprising one or more assigned user roles; providing an interface comprising folders for ultrasound exam objects, the folders comprising an inbox folder, a pending folder, and a flagged folder; providing an interface comprising tools for reviewing ultrasound exam objects; configuring a communications link with at least one ultrasound imaging system; importing via the communications link an ultrasound exam object comprising a worksheet and one or more images; performing an assignment routing operation comprising assigning the ultrasound exam object to a performing user, and routing via the computer network the ultrasound exam object to a performing user's inbox folder to be completed; performing an interpretation routing operation comprising routing via the computer network a completed ultrasound exam object to an attending user's inbox folder to be interpreted, and transferring the completed ultrasound exam object to a performing user's pending folder; and performing QA routing operation comprising routing via the computer network a completed ultrasound exam object to a QA reviewer's inbox folder to be reviewed, transferring the completed ultrasound exam object to the performing user's pending folder, and routing via the computer network a reviewed ultrasound exam object to a performing user's flagged folder if the QA reviewer user requests feedback.

Clause 54. The method of Clause 53, wherein the ultrasound exam object further comprises a type with a value of clinical or educational, wherein if the type has a value of educational the interpretation routing operation is suspended.

Clause 55. The method of any of Clauses 53-54, wherein the one or more images comprise at least one static image, at least one video image, or both at least one static image and least one video image.

Clause 56. The method of any of Clauses 53-55, wherein the worksheet comprises patient data and exam data.

Clause 57. The method of Clause 56, wherein the tools for reviewing ultrasound exam objects allow a user to: view the one or more images, review the worksheet, edit the worksheet, view the patient data, edit the patient data, view the exam data, edit the exam data, and perform QA review.

Clause 58. The method of any of Clauses 53-57, wherein one or more folders comprises a list view and a card view.

Clause 59. The method of Clause 58, wherein each card in the card view comprises an exam status icon.

Clause 60. The method of Clause 59, wherein the exam status icon indicates draft, pending, failed archive, educational, or archived status.

Clause 61. The method of any of Clauses 53-60, wherein the interface comprising folders for ultrasound exam objects comprises a search element.

Clause 62. The method of Clause 61, wherein the ultrasound exam object further comprises one or more tags.

Clause 63. The method of Clause 62, wherein the search element allows a user to search by tag.

Clause 64. The method of any of Clauses 53-63, wherein the interpretation routing operation and the QA routing operation are performed in series, wherein the interpretation routing operation is performed before the QA routing operation.

Clause 65. The method of any of Clauses 53-64, wherein the interpretation routing operation and the QA routing operation are performed in parallel.

Clause 66. The method of any of Clauses 53-65, wherein the method further comprises configuring a communications link with at least one electronic medical record (EMR) system.

Clause 67. The method of any of Clauses 53-66, wherein the method further comprises configuring a communications link with at least one electronic archive.

Clause 68. The method of Clause 67, wherein the method further comprises performing an archive routing operation comprising routing via the computer network the ultrasound exam object to the archive subsequent to completion, interpretation, and review.

Clause 69. The method of Clause 68, wherein the interface comprising folders for ultrasound exam objects further comprises an archived folder.

Clause 70. The method of Clause 68, wherein the archive comprises a picture archiving and communication system (PACS) or a vendor neutral archive (VNA).

Clause 71. The method of any of Clauses 53-70, wherein the method further comprises calculating metrics over a plurality of ultrasound exam objects, the metrics comprising quality and efficiency.

Clause 72. The method of Clause 71, wherein the method further comprises providing a user interface allowing a user to view the metrics.

Clause 73. The method of any of Clauses 53-72, wherein the user interface allowing an administrator user to assign user roles to other users further allows the administrator user to assign a point of care specialty and a facility to other users.

Clause 74. The method of Clause 73, wherein the assignment routing operation comprises assigning the ultrasound exam object to a performing user at least in part based on point of care specialty and facility.

Clause 75. The method of any of Clauses 53-74, wherein the interface comprising folders for ultrasound exam objects further comprises an unassigned folder.

Clause 76. The method of any of Clauses 53-75, wherein the interface comprising folders for ultrasound exam objects further comprises a favorites folder, and wherein the interface comprising tools for reviewing ultrasound exam objects further comprises an element to mark an ultrasound exam object as a favorite.

Clause 77. The method of any of Clauses 53-76, wherein the interface comprising folders for ultrasound exam objects further comprises a billed folder.

Clause 78. The method of Clause 77, wherein the interpretation routing operation further comprises routing via the computer network an interpreted and archived ultrasound exam object to an attending user's billed folder.

Clause 79. A platform for routing point of care ultrasound examinations in a computer network comprising any of the features or steps recited in any of the preceding Clauses.

Clause 80. A system for routing point of care ultrasound examinations in a computer network comprising any of the features or steps recited in any of the preceding Clauses.

Clause 81. A method comprising any of the features or steps recited in any of the preceding Clauses.

FURTHER CONSIDERATIONS

In some embodiments, any of the clauses herein may depend from any one of the independent clauses or any one of the dependent clauses. In accordance with some embodiments, any of the clauses (e.g., dependent or independent clauses) may be combined with any other one or more clauses (e.g., dependent or independent clauses). In accordance with some embodiments, a claim may include some or all of the words (e.g., steps, operations, means or components) recited in a clause, a sentence, a phrase or a paragraph. In accordance with some embodiments, a claim may include some or all of the words recited in one or more clauses, sentences, phrases or paragraphs. In accordance with some embodiments, some of the words in each of the clauses, sentences, phrases or paragraphs may be removed. In accordance with some embodiments, additional words or elements may be added to a clause, a sentence, a phrase or a paragraph. In accordance with some embodiments, the subject technology may be implemented without utilizing some of the components, elements, functions or operations described herein. In accordance with some embodiments, the subject technology may be implemented utilizing additional components, elements, functions or operations.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

As used herein, the term "comprising" indicates the presence of the specified integer(s), but allows for the possibility of other integers, unspecified. This term does not imply any particular proportion of the specified integers. Variations of the word "comprising," such as "comprise" and "comprises," have correspondingly similar meanings.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A platform for routing point of care ultrasound examinations in a computer network comprising:

a plurality of computing devices, each computing device comprising at least one processor and instructions executable by the at least one processor to provide a client application comprising:

a user role module configured to present a user interface allowing an administrator user to assign user roles to other users, the user roles comprising a performing user, an attending user, and a quality assurance (QA) reviewer user;

an ultrasound management module configured to present an interface comprising folders for ultrasound exam objects, the folders comprising an inbox folder, a pending folder, and a flagged folder; and an ultrasound review module configured to present an interface comprising tools for reviewing ultrasound exam objects; and at least one server processor and instructions executable by the at least one server processor to provide a server application comprising:

a data store comprising one or more assigned user roles;

an interface module configured to communicate with at least one ultrasound imaging system and import an ultrasound exam object, the ultrasound exam object comprising a worksheet and one or more images;

an assignment routing module configured to:

assign the ultrasound exam object to a performing user, and route via the computer network the ultrasound exam object to a performing user's inbox folder to be completed;

an interpretation routing module configured to:

route via the computer network a completed ultrasound exam object to an attending user's inbox folder to be interpreted, and transfer the completed ultrasound exam object to a performing user's pending folder; and a QA routing module configured to:

route via the computer network a completed ultrasound exam object to a QA reviewer's inbox folder to be reviewed, transfer the completed ultrasound exam object to the performing user's pending folder, and route via the computer network a reviewed ultrasound exam object to a performing user's flagged folder if the QA reviewer user requests feedback.

2. The platform of claim 1, wherein the ultrasound exam object further comprises a type with a value of clinical or educational, wherein if the type has a value of educational the interpretation routing operation is suspended.

3. The platform of claim 1, wherein the one or more images comprise at least one static image, at least one video image, or both at least one static image and least one video image.

4. The platform of claim 1, wherein the interpretation routing module and the QA routing module operate in series, wherein the interpretation routing module operates before the QA routing module.

5. The platform of claim 1, wherein the interpretation routing module and the QA routing module operate in parallel.

6. The platform of claim 1, wherein the server application further comprises an interface module configured to communicate with at least one electronic medical record (EMR) system.

7. A computer-implemented system for routing point of care ultrasound examinations in a computer network comprising at least one processor and instructions executable by the at least one processor to provide an application comprising:

a user role module configured to present a user interface allowing an administrator user to assign user roles to other users, the user roles comprising a performing user, an attending user, and a quality assurance (QA) reviewer user;

a data store comprising one or more assigned user roles;

an ultrasound management module configured to present an interface comprising folders for ultrasound exam objects, the folders comprising an inbox folder, a pending folder, and a flagged folder;

an ultrasound review module configured to present an interface comprising tools for reviewing ultrasound exam objects;

an interface module configured to communicate with at least one ultrasound imaging system and import an ultrasound exam object, the ultrasound exam object comprising a worksheet and one or more images;

an assignment routing module configured to: assign the ultrasound exam object to a performing user, and route via the computer network the ultrasound exam object to a performing user's inbox folder to be completed;

an interpretation routing module configured to: route via the computer network a completed ultrasound exam object to an attending user's inbox folder to be interpreted, and transfer the completed ultrasound exam object to a performing user's pending folder; and a QA routing module configured to: route via the computer network a completed ultrasound exam object to a QA reviewer's inbox folder to be reviewed, transfer the completed ultrasound exam object to the performing user's pending folder, and route via the computer network a reviewed ultrasound exam object to a performing user's flagged folder if the QA reviewer user requests feedback.

8. The system of claim 7, wherein the ultrasound exam object further comprises a type with a value of clinical or educational, wherein if the type has a value of educational the interpretation routing operation is suspended.

9. The system of claim 7, wherein the one or more images comprise at least one static image, at least one video image, or both at least one static image and least one video image.

10. The system of claim 7, wherein the interface comprising folders for ultrasound exam objects comprises a search element.

11. The system of claim 7, wherein the interpretation routing module and the QA routing module operate in series, wherein the interpretation routing module operates before the QA routing module.

12. The system of claim 7, wherein the application further comprises an interface module configured to communicate with at least one electronic medical record (EMR) system.

13. The system of claim 7, wherein the application further comprises an insights module configured to calculate metrics over a plurality of ultrasound exam objects, the metrics comprising quality and efficiency.

14. A computer-implemented method of routing point of care ultrasound examinations in a computer network comprising:

providing a user interface allowing an administrator user to assign user roles to other users, the user roles comprising a performing user, an attending user, and a quality assurance (QA) reviewer user;

maintaining a data store comprising one or more assigned user roles;

providing an interface comprising folders for ultrasound exam objects, the folders comprising an inbox folder, a pending folder, and a flagged folder;

providing an interface comprising tools for reviewing ultrasound exam objects;

configuring a communications link with at least one ultrasound imaging system;

importing via the communications link an ultrasound exam object comprising a worksheet and one or more images;

performing an assignment routing operation comprising assigning the ultrasound exam object to a performing user, and routing via the computer network the ultrasound exam object to a performing user's inbox folder to be completed;

performing an interpretation routing operation comprising routing via the computer network a completed ultrasound exam object to an attending user's inbox folder to be interpreted, and transferring the completed ultrasound exam object to a performing user's pending folder; and performing QA routing operation comprising routing via the computer network a completed ultrasound exam object to a QA reviewer's inbox folder to be reviewed, transferring the completed ultrasound exam object to the performing user's pending folder, and routing via the computer network a reviewed ultrasound exam object to a performing user's flagged folder if the QA reviewer user requests feedback.

15. The method of claim 14, wherein the ultrasound exam object further comprises a type with a value of clinical or educational, wherein if the type has a value of educational the interpretation routing operation is suspended.

16. The method of claim 14, wherein the one or more images comprise at least one static image, at least one video image, or both at least one static image and least one video image.

17. The method of claim 14, wherein the worksheet comprises patient data and exam data.

18. The method of claim 14, wherein the interpretation routing operation and the QA routing operation are performed in series, wherein the interpretation routing operation is performed before the QA routing operation.

19. The method of claim 14, wherein the method further comprises configuring a communications link with at least one electronic medical record (EMR) system.

20. The method of claim 14, wherein the interface comprising folders for ultrasound exam objects further comprises a favorites folder, and wherein the interface comprising tools for reviewing ultrasound exam objects further comprises an element to mark an ultrasound exam object as a favorite.

\* \* \* \* \*